United States Patent [19]

Wachter et al.

[11] Patent Number: 4,761,413
[45] Date of Patent: Aug. 2, 1988

[54] 1,5-EPOXY-2,3,4,5-TETRAHYDRO-1H-3-BENZAZEPINS AND USE IN TREATMENT OF ULCERS

[75] Inventors: Michael P. Wachter, Bloomsbury; Donald S. Karanewsky, East Winsor, both of N.J.

[73] Assignee: Ortho Pharmaceutical Corporation, Raritan, N.J.

[21] Appl. No.: 945,273

[22] Filed: Dec. 22, 1986

[51] Int. Cl.[4] .................. A61K 31/535; C07D 498/08
[52] U.S. Cl. .................................. 514/229.8; 544/101
[58] Field of Search ................ 544/101; 514/232, 237, 514/239

[56] References Cited

PUBLICATIONS

Fisera et al., Chemical Abstracts, vol. 102 (1985) 149018u.

Primary Examiner—Richard L. Raymond
Attorney, Agent, or Firm—Benjamin F. Lambert

[57] ABSTRACT

The synthesis of epoxybenzazepin compounds is described. The novel compounds have anti-ulcer activity.

8 Claims, No Drawings

1,5-EPOXY-2,3,4,5-TETRAHYDRO-1H-3-BENZAZEPINS AND USE IN TREATMENT OF ULCERS

BACKGROUND OF THE INVENTION

1. Field of the Invention

The present invention relates to novel 1,5-epoxy-2,3,4,5-tetrahydro-1H-3-benzazepins as described further below. The benzazepins are useful as anti-ulcer agents.

2. Description of the Prior Art

Several benzazepin compounds have been previously described which have a variety of biological activities. For example, U.S. Pat. No. 4,197,207 describes 1-phenyl-2,3,4,5-tetrahydro-1H-3-benzazepins, particularly the 1-(4-hydroxyphenyl)-6-chloro-7,8-dihydroxy derivatives, which are antihypertensive agents by virtue of their renal vasodilating activity.

J. Med. Chem. 23, 975 (1980) describes compounds such as 1-phenyl-7,8-dihydroxy-2,3,4,5-tetrahydro-1H-3-benzazepins which are agonists of dopamine receptors and 6-phenylthio-7,8-dihydroxy-3-methyl-2,3,4,5-tetrahydro-1H-3-benzazepins which are dopamine receptor antagonists and neuroleptics.

U.S. Pat. No. 3,393,192 discloses that certain 7,8-disubstituted -3-methyl-2,3,4,5-tetrahydro-1H-3-benzazepins, such as the 7,8-dimethoxy derivatives, are useful as antipsychotic agents.

A series of 2,2-dimethyl-7,8-disubstituted-1-phenyl-2,3,4,5-tetrahydro-1H-3-benzazepins, such as the 7,8-dimethoxy derivatives, have been reported in J. Heterocyclic Chem. 16, 1525 (1979) to have anti-arrhythmic activity and are thus useful as cardiovascular agents. The phenyl may optionally be substituted.

Finally, J. Med. Chem. 22, 455 (1979) describes 1,5-methano-3-substituted-2,3,4,5-tetrahydro-1H-3-benzazepins which have very weak or no analgesic activity.

None of the 2,3,4,5-tetrahydro-1H-3-benzazepins of the prior art discussed above are reported to have anti-ulcer activity, and none of these compounds have a 1,5-epoxy substitutent.

SUMMARY OF THE INVENTION

The present invention is directed to benzazepin compounds of the formula

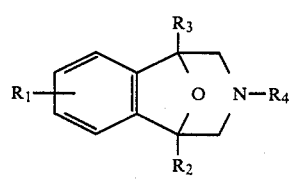

where $R_1$ may be H, 7-halogen, 7,8-dihydroxy, 7,8-methylenedioxy, 7,8-di-$C_1$-$C_3$ alkoxy or 7,8-dibenzyloxy;

$R_2$ may be H, 1,3-dioxolanyl, phenyl or phenyl substituted by $CF_3$, $C_1$-$C_6$ alkyl or $C_1$-$C_4$ alkoxy;

$R_3$ may be H, phenyl or phenyl substituted by $CF_3$, $C_1$-$C_6$ alkyl or $C_1$-$C_4$ alkoxy;

$R_4$ may be H, benzyl, $C_1$-$C_6$ alkyl, $C_3$-$C_6$ alkenyl, —(CH$_2$)$_3$OH, —COR$_5$,

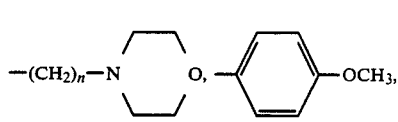

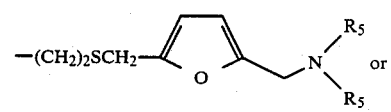

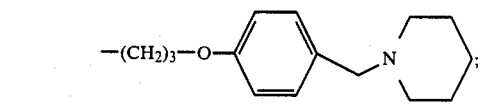

$R_5$ may be $C_1$-$C_3$ alkyl; and n may be 2 or 3; provided that when $R_1$ is 7-halogen, $R_4$ is not hydrogen.

The compounds of formula I are useful as anti-ulcer agents. Several of the compounds have both cytoprotective and anti-secretory properties. In addition, some of the compounds possess an antiarrhythmic activity.

DETAILED DESCRIPTION OF THE INVENTION

The invention in its broadest aspects relates to benzazepin compounds which have anti-ulcer activity. The benzazepin compounds of the invention demonstrating an anti-ulcer activity are shown by formula I above. The novel benzazepin compounds having this activity contain a 1,5-epoxy substituent.

The preferred compounds of the present invention are those wherein $R_1$ is H, $R_2$ is phenyl or 3-trifluoromethylphenyl, $R_3$ is H and $R_4$ is H,

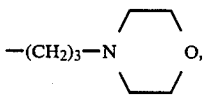

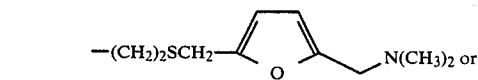

The compounds of formula I can be prepared as shown in Scheme 1.

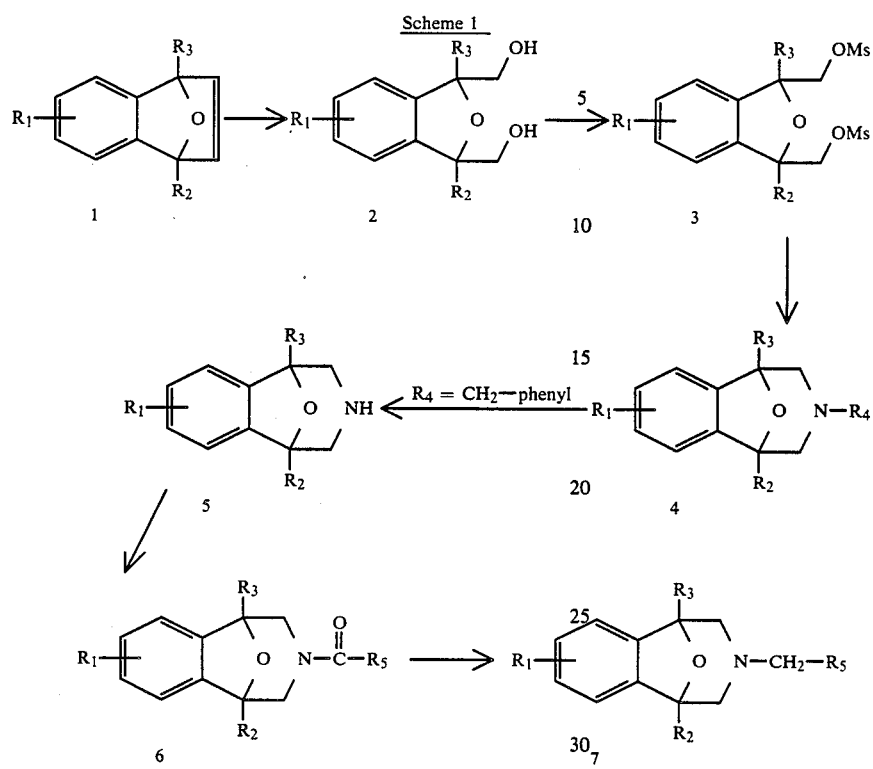

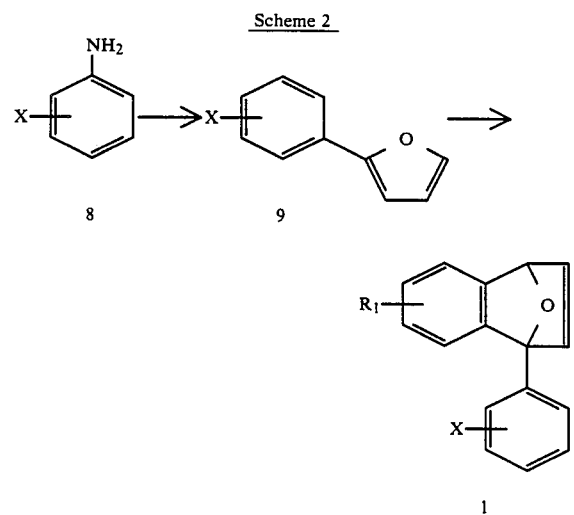

The olefin 1, which is prepared as described below in an inert solvent, such as methylene chloride or a mixture of methylene chloride and methanol, is subjected to ozonolysis by passing ozone into the solution until a pale blue or pale blue-green color is obtained. The solution is then transferred to a solution of LiAlH$_4$ in an inert solvent such as tetrahydrofuran at 0° C. under nitrogen. The resulting solution is warmed to room temperature and refluxed for about 0.5–5 hours. In addition, nitrogen can first be passed through the ozonolyzed solution prior to transfer to the LiAlH$_4$ solution. Alternatively, nitrogen is passed through the ozonolyzed solution and dimethylsulfide is added at −78° C. The mixture is gradually warmed to room temperature and the solvents removed. The residue is taken up in an inert solvent such as tetrahydrofuran and added to a solution of LiAlH$_4$ in tetrahydrofuran. The mixture is refluxed for about 0.5–1.5 hours. The diol 2 is recovered from the refluxed material by successive treatment with water, 15% NaOH and water.

The diol 2 is taken up in an inert solvent such as methylene chloride which contains an amine such as trimethylamine. Methanesulfonyl chloride in an inert solvent such as methylene chloride is added to this mixture at 0° C. and stirred for 15–60 minutes. The mixture is poured into ice containing 2N HCl and extracted with methylene chloride to produce crude dimesylate 3 which can be purified if desired. The dimesylate (Ms) 3 is heated with the amine R$_4$—NH$_2$ under nitrogen at about 70°–150° C. for about 0.5–5 hours to produce the epoxybenzazepin 4. Alternatively, the dimesylate is heated with the amine to form the aminomesylate and then treated with base (K$_2$CO$_3$) in dimethylformamide to yield the epoxybenzazepin 4.

When R$_4$ is benzyl, the epoxybenzazepin 4 is hydrogenated by treatment with H$_2$/Pd to produce the epoxybenzazepin 5 where R$_4$ is H. The epoxybenzazepin 6 where R$_4$ is —COR$_5$ is prepared by treating compound 5 with the appropriate anhydride, (R$_5$CO)$_2$O. The epoxybenzazepin 7 is obtained by treating compound 6 with LiAlH$_4$ as described above.

The starting olefin 1 can be prepared as shown in Schemes 2–4.

The phenylfuran 9 is prepared from an appropriately substituted aniline 8 by aprotic diazotization with i-amylnitrite in furan as described in *J. Chem. Soc. (B)*, 1253 (1969), wherein X is CF$_3$, lower alkyl and lower alkoxy. The olefin 1 is prepared from phenylfuran 9 by refluxing compound 9 and i-amylnitrite in an inert solvent such as tetrahydrofuran and slowly adding anthranilic acid.

Scheme 3

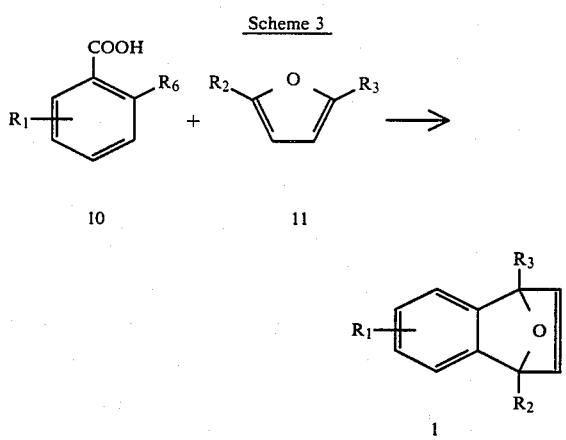

When R₆ is NH₂, the substituted anthranilic acid 10 in an inert solvent such as tetrahydrofuran is added to a refluxing solution of i-amylnitrite and furan 11 in an inert solvent such as tetrahydrofuran to produce the olefin 1.

Alternatively, where R₆ is N₂⁺Cl⁻, a suspension of the substituted benzoic acid 10 in a solution of the furan 11, propylene oxide and solvent such as 1,4-dichlorobutane is heated at 135°–145° C. for about 2.5 hours.

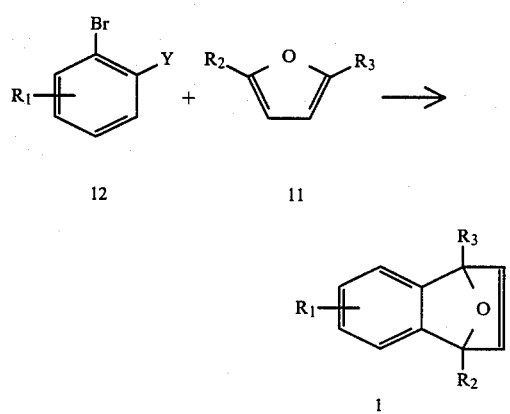

A solution of dihalobenzene 12, where Y is I, in a mixture of furan 11 and a solvent such as ether at −78° C. under nitrogen, is treated with n-butyl lithium for about 1.5–3.5 hours. The mixture is then warmed to room temperature and further reacted for about 1–3 hours to produce the olefin 1. Alternatively, a solution of the dihalobenzene 12, where Y is F and R₁ is H, in an inert solvent such as tetrahydrofuran is slowly added to a refluxing mixture of furan 11 and magnesium turnings in an inert solvent such as tetrahydrofuran under N₂ and refluxed for about 0.5–2 hours to produce the olefin 1.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 0.2 to about 200 mg/kg, and preferably from about 2.0 to about 50 mg/kg of the active ingredient.

The following examples describe the invention in greater particularity and are intended to be a way of illustrating but not limiting the invention.

EXAMPLE 1

3-Benzyl-1,5-epoxy-1-[(3-trifluoromethyl)phenyl]-1,2,4,5-tetrahydro-3-benzazepin oxalate A solution of 3-trifluoromethyl aniline (30 ml, 0.24M) and i-amylnitrite (48.4 ml, 0.36M) in furan (350 ml) was stirred at room temperature for 24 hours under N₂. The mixture was then washed with H₂O and saturated NaCl, dried (Na₂SO₄) and evaporated. The residue was chromatographed on neutral alumina (activity II), eluting with hexane, to give an orange liquid (13.3 g, 26% yield). NMR (CDCl₃) δ 6.40 (m, 1H, furan-$\underline{H}_4$), 6.65 (d, 1H, J=4 Hz, furan-$\underline{H}_3$), 7.30–7.90 (m, 5H, aromatic $\underline{H}$ and furan-$\underline{H}_5$).

Anthranilic acid (10.8 g, 0.079M, recrystallized from benzene) in dry THF (150 ml) was added dropwise to a refluxing solution of the above product (13.3 g, 0.063M) and i-amylnitrite (17 ml, 0.095M) in dry THF (100 ml) under N₂. After the addition was complete, refluxing was continued for 0.5 hour. The reaction mixture was evaporated and the residue taken up in ether. The ether solution was washed with several portions of saturated NaHCO₃, H₂O, saturated NaCl, dried (Na₂SO₄) and evaporated. The residue was purified by column chromatography on neutral alumina (activity II) eluting with hexane, then 1:6 ether:hexane, then 1:2 ether/hexane. Fractions containing the desired compound were combined and concentrated to give an orange liquid. (9.64 g, 53% yield). NMR (CDCl₃) δ 5.90 ppm (s, 1H, ArC$\underline{H}$O), 6.85–8.00 (m, 10H, aromatic $\underline{H}$ and —C$\underline{H}$=C$\underline{H}$—).

Ozone was passed into a solution of this product (9.6 g, 0.033M) in CH₂Cl₂ (200 ml) at −78° C. (dry ice-acetone bath) until a pale blue color was obtained. Nitrogen was then passed into the solution to discharge the blue color. The solution was then transferred by cannulus to a solution of LiAlH₄ (3.14 g, 0.083M) in dry THF (150 ml) at 0° C. When the addition was complete, the mixture was refluxed for an additional 1.5 hours. It was cooled in an ice bath and treated successively with distilled H₂O (3.1 ml), 15% NaOH solution (3.1 ml) and H₂O (9.3 ml) in a dropwise manner. The resulting suspension was filtered through Celite, dried (Na₂SO₄) and concentrated in vacuo to give the diol intermediate (9.27 g, 87% yield).

A solution of methanesulfonyl chloride (5.54 ml, 0.072M) in CH₂Cl₂ (25 ml) was added dropwise to a solution of the diol (9.27 g, 0.029M) and triethylamine (11.9 ml, 0.086M) in CH₂Cl₂ (150 ml) at 0° C. After 30 minutes, the mixture was poured onto ice containing 2N HCl (75 ml) and extracted with CH₂Cl₂. The extracts were washed with H₂O, dried (Na₂SO₄) and the solvent removed in vacuo to give the dimesylate intermediate (14.5 g, 100% yield).

The dimesylate (9.0 g, 0.019M) was heated with benzylamine (16 ml) at 120° C. for one hour under N₂. The excess benzylamine was distilled in vacuo and the residue partitioned between CH₂Cl₂ and H₂O. The CH₂Cl₂ extract was washed with H₂O, dried (Na₂SO₄) and evaporated. The residue was purified by column chromatography on silica gel, eluting with 1:5 ether/hexane to give the epoxy benzazepin (4.5 g, 61% yield). A solution of oxalic acid (2.4 g, 0.019M) in ether was added dropwise to a solution of the product (4.5 g, 0.011M) in ether to give the named compound, which was recrystallized from MeOH/Et₂O (3.6 g, 67% yield), mp 196.5°–199° C. (dec). NMR (DMSO-d₆) δ 2.60 ppm (broad s, 4H, —CH₂—N—CH₂), 3.25–3.60 (m, 2H, NCH₂Ph), 5.35 (s, 1H, ArCHO), 6.70–7.90 (m, 13H, aromatic H), 9.30 [m, 2H, (2x) CO₂H]. MS: 395 (M+), 91 (BP). IR (KBr): 3400 cm⁻¹ (OH), 1720 cm⁻¹ (CO₂H), 1625 cm⁻¹ (CO₂⊖).

Theor. C₂₄H₂₀NOF₃·C₂H₂O₄: C, 64.33; H, 4.57; N, 2.89. Found: C, 63.90; H, 4.67; N, 2.92.

EXAMPLE 2

1,5-Epoxy-1-[(3-trifluoromethyl)phenyl]-1,2,4,5-tetrahydro-3-benzazepin oxalate A solution of the compound of Example 1 in EtOH (150 ml) and AcOH (15 ml) was hydrogenated (1.2 g, 10% Pd-C) in a Parr apparatus at an initial pressure of 40 psi overnight. The resulting solution was treated with aqueous NaOH, filtered through Celite and evaporated to give the epoxybenzazepin as an oil.

A solution of oxalic acid (0.83 g, 0.007M) in ether was added dropwise to a solution of this product in ether to give the named compound as a white precipitate. The solid was collected and then recrystallized from MeOH/acetone (2.0 g, 84% yield); mp 205°–206° C. (dec). NMR (DMSO-d₆) δ 2.80–3.95 ppm (m, 4H, CH₂—N—CH₂), 5.60 (s, 1H, ArCHO), 6.80–8.00 (m, 8H, aromatic H), 9.05 [s, 3H, (2x) CO₂H, NH]. MS: 305 (M+), 77 (BP). IR (KBr): 3400 cm⁻¹ (OH), 1720 cm⁻¹ (CO₂H), 1610 cm⁻¹ (CO₂⁻).

Theor. C₁₇H₁₄NOF₃·C₂H₂O₄: C, 57.73; H, 4.08; N, 3.54. Found: C, 57.59; H, 4.20; N, 3.56.

EXAMPLE 3

1,5-Epoxy-3-[N-(3-morpholinopropyl)]-1-[(3-trifluoromethyl)phenyl]-1,2,4,5-tetrahydro-3-benzazepin dioxalate The dimesylate (5.7 g, 0.012M), prepared as described in Example 1, was heated with N-(3-aminopropyl)morpholine (15 ml) at 130° C. for three hours under N₂. Under cooling, excess N-(3-aminopropyl)morpholine was removed in vacuo and the product was taken up in CH₂Cl₂, washed twice with H₂O, saturated NaCl, dried (Na₂SO₄) and evaporated. The residue was purified by column chromatography on silica gel eluting with 1:2 ether/hexane, then 5% MeOH/CH₂Cl₂. Fractions containing the desired compound were combined and concentrated to give the epoxy benzazepin. A solution of oxalic acid (1.7 g, 0.013M) in ether was added dropwise to a solution of this product in ether to give the titled compound, which was recrystallized from MeOH/acetone as a white powder (3.50 g, 48% yield), mp 206°–207° C. NMR (DMSO-d₆) δ 1.70 ppm (m, 2H, —CH₂CH₂CH₂—), 2.40–3.90 [m, 16H, (6x) —N—CH₂, CH₂OCH₂], 5.40 (s, 1H, ArCHO), 6.80–7.85 (m, 8H, aromatic H), 11.00 [s, 4H, (4x) COOH]. MS: 432 (M+). IR (KBr): 3420 cm⁻¹ (OH), 1710 cm⁻¹ (CO₂H), 1620 cm⁻¹ (CO₂).

Theor. C₂₄H₂₇N₂O₂F₃·C₄H₄O₈: C, 54.90; H, 5.10; N, 4.57. Found: C, 54.75; H, 5.31; N, 4.31.

EXAMPLE 4

3-[3-[[3-(1-Piperidinyl)methyl]phenoxy]propyl]-1,5-epoxy-1-(3-trifluoromethyl)phenyl-1,2,4,5-tetrahydro-3-benzazepin dioxalate monohydrate The dimesylate (6.5 g, 13.32 mM), prepared as described in Example 1, was heated with piperidinylmethylphenoxy amine (18 ml) at 130° C. for four hours, and room temperature for 12 hour. The resulting sticky oil was treated with Et₂O and filtered. The filtrate was concentrated in vacuo and was purified via Kieselgel-60 (500 g) column chromatography, eluted with 2.5% MeOH/CH₂Cl₂ to afford pure epoxybenzazepin (oil, 4.0 g, 56% yield). NMR (CDCl₃) 1.6 (m, 8H, piperidinyl-H₃,₄,₅, —CH₂CH₂CH₂—), 2.47 (m, 10H, piperidinyl-H₂,₆, N—CH₂), 3.33 (m, 4H, CH₂—Ar, OCH₂CH₂), 5.2 (s, 1H, ArCHO), 6.2–7.8 (m, 12H, aromatic H).

A solution of this product (2.32 g, 4.32 mM) in MeOH (1 ml) and Et₂O (500 ml) was treated with two equivalents of anhydrous oxalic acid in Et₂O to give the crude oxalate salt which was filtered. Recrystallization from EtOH/Et₂O (75/0.5 ml) afforded pure named compound (white solids, 2.13 g, 69% yield), mp 165°–167° C. NMR (DMSO-d₆) δ 0.63 (br s, 6H, piperidinyl-H₃,₄,₅), 5.4 (s, 1H, ArCH—O), 6.67–8.0 (brm, 12H, aromatic-H), 10.0 (br s, 2CO₂H); MS: 536 (M+).

Theor. C₃₆H₃₉F₃N₂O₁₀·H₂O: C, 58.85; H, 5.63; N, 3.81. Found: C, 58.91; H, 5.43; N, 3.62.

EXAMPLE 5

3-[2-[[[5-(Dimethylamino)methyl-2-furanyl]methylthio]ethyl]-1,5-epoxy-1-[3-trifluoromethyl)phenyl-1,2,4,5-tetrahydro-3-benzazepin dioxalate The dimesylate (6.23 g, 12.97 mM), prepared as described in Example 1, was heated with 2-[(5-dimethylaminomethyl-2-furanyl)methylthio]ethylamine (18 ml), prepared as described in Belgian Pat. No. 857,388, at 130° C. for four hours, and room temperature for 17 hours. The resulting sticky oil was treated with Et₂O, and filtered. The filtrate was concentrated in vacuo to give crude product which was purified via Kieselgel-60 (800 g) column chromatography, eluted with 3% MeOH/CH₂Cl₂ to afford pure epoxy benzazepin (oil, 1.89 g, 29% yield). NMR (CDCl₃) δ 2.2 (s, 6H, N(CH₃)₂), 2.5 (bm, 2H, —NCH₂), 2.77 (bs, 2H, SCH₂), 3.42 (s, 2H, furan CH₂N), 5.27 (m, 1H, CHO), 5.97 (dd, 2H, furan-H₃ and —H₄), 7.0–7.8 (m, 8H, aromatic H).

A solution of this product (694.7 mg, 1.38 mM) in MeOH (1 ml) and Et₂O (280 ml) was treated with two equivalents of anhydrous oxalic acid in Et₂O to give the crude oxalate salt which was filtered. Recrystallization from EtOH/Et$_2$O (75/0.5 ml) afforded pure titled compound (white solids, 433 mg, 46% yield), mp 165°–166° C. NMR (DMSO-d$_6$) δ 5.2 (bs, 1H, HCO), 6.2 (d, 1H, furan-H$_3$), 6.53 (d, 1H, furan-H$_4$), 6.67–8.0 (m, 8H, aromatic H). MS: 484 (M+).

Theor. C$_{27}$H$_{29}$F$_3$N$_2$O$_2$S.C$_4$H$_4$O$_8$: C, 54.54; H, 4.87; N, 4.10. Found: C, 54.22; H, 4.95; N, 3.90.

EXAMPLE 6

3-Benzyl-1,5-epoxy-1-phenyl-1,2,4,5-tetrahydro-3-benzazepin

A solution of aniline (12.5 g, 0.134M) and i-amylnitrite (27.5 ml, 0.205M) in furan (400 ml) was stirred at 30° C. (bath temperature) for 24 hours under N$_2$. The mixture was then washed with water and saturated NaCl solution, dried over anhydrous Na$_2$SO$_4$ and evaporated. The brown residue was filtered through a short column of neutral alumina (activity grade II) using pentane as an eluent. The fractions were combined and concentrated and the residue distilled in vacuo to give pure 2-phenylfuran (7.65 g, 39% yield), bp 51°–54° C. (1.0 mm). NMR (CDCl$_3$) δ 6.45 ppm (dd, 1H, J=1.5, 3.0 Hz, furan-H$_4$), 6.62 (d, 1H, J=4.0 Hz, furan-H$_3$), 7.2–7.8 (m, 6H, phenyl and furan-H$_5$).

Anthranilic acid (18.8 g, 0.137M, recrystallized from benzene) in dry THF (100 ml) was added dropwise over two hours to a refluxing solution of the 2-phenylfuran (17.98 g, 0.125M) and freshly distilled i-amylnitrite (23.5 ml, 0.175M) in dry THF (100 ml) under nitrogen. After the addition was complete, refluxing was continued for one hour. The reaction mixture was evaporated to dryness and the dark brown residue taken up in Et$_2$O. The Et$_2$O solution was washed with several portions of saturated NaHCO$_3$ solution and the combined washings re-extracted with Et$_2$O. The Et$_2$O extracts were combined and washed successively with distilled water and saturated NaCl solution, dried over anhydrous Na$_2$SO$_4$ and concentrated in vacuo. The residue was purified on neutral Al$_2$O$_3$ (activity grade II) eluting with hexane, then hexane/CH$_2$Cl$_2$ (1:6) and finally hexane-CH$_2$Cl$_2$ (1:1). All fractions containing the desired compound were combined and concentrated. The residue was crystallized from hexane to give the olefin (15.34 g, 56% yield) as pale yellow crystals, mp 115°–117° C. NMR (CDCl$_3$) δ 5.75 ppm (broad s, 1H,

ArCHO—), 6.8–7.8 (m, 11H, —CH=CH— and aromatic H). MS: 220 (M+).

Ozone was passed into a solution of the olefin (15.24 g, 0.069M) in 1:1 methanol-CH$_2$Cl$_2$ (500 ml) at −78° C. (dry ice-acetone bath) until a pale blue color was obtained. Nitrogen was then passed into the solution to discharge the blue color and Me$_2$S (20 ml, 0.273M) was added. After stirring at −78° C. for 45 minutes, 0° C. (ice bath) for 30 minutes, and room temperature for 30 minutes, the methanol was removed in vacuo. Benzene (~100 ml) was added and the mixture again evaporated to dryness.

The residue was taken up in dry THF (150 ml) and added dropwise to a suspension of LiAlH$_4$ (6.95 g, 0.183M) in dry THF (150 ml) at 0° C. (ice bath). When the addition was complete, the mixture was allowed to warm to room temperature and then refluxed for 45 minutes. The mixture was then cooled in an ice bath and treated successively with distilled water (7.0 ml), 15% NaOH solution (7.0 ml) and water (21.0 ml) in a dropwise manner. The resulting white suspension was filtered through Celite, the filtrate washed thoroughly with THF, and the combined washings concentrated in vacuo. The residue was crystallized from Et$_2$O/hexane to give the diol (16.85 g, 95% yield) as white crystals, mp 150°–152° C. A sample (1.55 g) was recrystallized from EtOAc/hexane to give pure diol (1.24 g) as white plates, mp 153°–153.5° C. NMR (d$_6$-acetone) δ 3.80–4.50 [m, 6H, (2x) CH$_2$OH], 5.47 (t, 1H, J=3 Hz, ArCHO—), 7.20–7.80 (m, 9H, aromatic H). IR (KBr): 3300 cm$^{-1}$ (OH). MS: 256 M+).

A solution of methanesulfonyl chloride (7.6 ml, 98.2 mM) in CH$_2$Cl$_2$ (25 ml) was added drowpise to a solution of the diol (10.01 g, 39.1 mM) and triethylamine (16.5 ml, 119.3 mM) in CH$_2$Cl$_2$ (115 ml) at 0° C. (ice bath). When the addition was complete, the mixture was stirred at 0° C. for 30 minutes and then poured onto ice containing 50 ml of 2N HCl solution. The organic layer was separated, washed with saturated NaCl solution, dried over anhydrous Na$_2$SO$_4$ and solvent removed in vacuo to give crude dimesylate.

The crude dimesylate was treated with freshly distilled benzylamine (20.0 ml, 183.4 mM) and heated at 100° C. for two hours under nitrogen. The excess benzylamine was distilled off in vacuo and the residue partitioned between CH$_2$Cl$_2$ and distilled water. The CH$_2$Cl$_2$ extract was then dried over anhydrous Na$_2$SO$_4$ and concentrated in vacuo to give crude amino-mesylate which was dissolved in DMF (100 ml), treated with finely powdered anhydrous K$_2$CO$_3$ (40.0 g, 0.290M) and refluxed for 3.5 hours under nitrogen. The cooled mixture was diluted with ether and filtered. The filtered solution was then washed with several portions of distilled water and the combined aqueous washings re-extracted with ether. The combined ether extract was washed with saturated NaCl solution, dried over anhydrous K$_2$CO$_3$ and the ether removed by vacuo. The residue (13.3 g) was purified by column chromatography on 400 g silica gel and eluted with Et$_2$O/hexane (1:10). The benzazepin (10.84 g, 85% yield) from the diol was thus isolated as a pale yellow oil. The oil was crystallized from hexane to give the named compound (10.43 g) as white crystals, mp 100°–101° C. NMR (CDCl$_3$) δ 2.72 ppm (AB doublet, 1H, J=10 Hz,

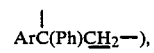
ArC(Ph)CH$_2$—), 2.75 (d, 2H, J=2 Hz,

ArCHCH$_2$—), 3.25 (AB doublet, 1H, J=10 Hz,

ArC(Ph)CH$_2$—), 5.25 (t, 1H, J=2 Hz,

6.70–7.70 (m, 9H, aromatic H). MS: 327 (M+).

Theor. C$_{23}$H$_{21}$NO: C, 84.37; H, 6.46; N, 4.28. Found: C, 84.67; H, 6.65; N, 4.31.

EXAMPLE 7

1,5-Epoxy-1-phenyl-1,2,4,5-tetrahydro-3-benzazepin

A suspension of 10% Pd-C (1.55 g) in a solution of the compound of Example 6 (5.18 g, 15.84 mM) and glacial acetic acid (20 ml) in absolute ethanol (200 ml) was hydrogenated in a Parr apparatus at an initial pressure of 32 psi. After 3.75 hours, the catalyst was filtered through Celite and the solvents removed in vacuo. The residue was taken up in CH$_2$Cl$_2$ and washed with saturated NaHCO$_3$. The aqueous washings were re-extracted with CH$_2$Cl$_2$ and the combined CH$_2$Cl$_2$ extracts dried over anhydrous Na$_2$SO$_4$ and evaporated. The residue (3.87 g) was crystallized from Et$_2$O/hexane to give crude product (3.60 g, 96% yield) as off-white crystals. The crude product was recrystallized from hexane to give pure titled compound (2.71 g) as white plates, mp 91°–92° C. NMR (CDCl$_3$) δ 1.57 ppm (broad s, 1H, NH), 2.63 (AB doublet, 1H, J=12 Hz,

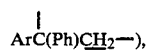

3.23 (AB quartet, 2H, J=14 Hz,

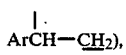

3.33 (AB doublet, 1H, J=12 Hz,

5.23 (broad s, 1H,

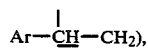

6.90–7.70 (m, 9H, aromatic H). IR (KBr): 3320 cm$^{-1}$ (NH), MS: 237 (M+).

Theor. C$_{16}$H$_{15}$NO: C, 80.98; H, 6.37; N, 5.90. Found: C, 81.00; H, 6.38; N, 5.84.

EXAMPLE 8

3-Acetyl-1,5-epoxy-1-phenyl-1,2,4,5-tetrahydro-3-benzazepin

A solution of the compound from Example 7 (1.30 g, 5.485 mM) in acetic anhydride (6.0 ml) was stirred at room temperature for 15 minutes. The mixture was then evaporated to dryness (vacuum pump) and the residue crystallized from Et$_2$O to give the named compound (1.43 g, 93% yield) as white crystals, mp 143°–144° C. NMR (CDCl$_3$) δ 1.78 and 1.82 ppm ([(2x)s, total of 3H, —COCH$_3$ (mixture of rotational isomers*)], 3.10–5.10 (m, 4H,

CH$_2$—N—CH$_2$), 5.36 (broad m, 1H,

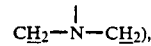

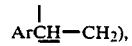

6.80–7.70 (m, 9H, aromatic H). IR (KBr): 1635 cm$^{-1}$. MS: 279 (M+),

* For a review of hindered rotational isomerism in the NMR of amides, see W. E. Stewart and T. H. Siddall, Chem. Rev. 70, 517 (1970).

Theor. C$_{18}$H$_{17}$NO$_2$: C, 77.40; H, 6.13; N, 5.01. Found: C, 77.55; H, 6.17; N, 4.86.

EXAMPLE 9

3-Ethyl-1-phenyl-1,5-epoxy-1,2,4,5-tetrahydro-3-benzazepin

To a suspension of LiAlH$_4$ (910 mg, 23.95 mM) in dry THF (40 ml) under N$_2$ was added the compound from Example 8 (2.22 g, 7.96 mM) in one portion and the resulting mixture refluxed for one hour. The mixture was then cooled in an ice bath and treated successively with distilled water (0.9 ml), 15% NaOH solution (0.9 ml) and water (2.7 ml) in a dropwise manner. The resulting white suspension was filtered through Celite, the filtrate washed thoroughly with THF, and the combined washings concentrated in vacuo. The residue was recrystallized from hexane to give the titled compound (1.89 g, 90% yield) as white crystals, mp 132°–134° C. NMR (CDCl$_3$) δ 0.90 ppm (t, 3H, NCH$_2$CH$_3$), 2.43 (q, 2H, J=7 Hz, NCH$_2$CH$_3$), 2.63 (AB doublet, 1H, J=11 Hz,

2.72 (m, 2H, 3.25 (AB doublet, 1H, J=11 Hz,

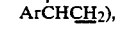

5.20 (broad t, 1H,

6.70–7.70 (m, 9H, aromatic H). MS: 265 (M+).

Theor. C$_{18}$H$_{19}$NO: C, 81.48; H, 7.22; N, 5.28. Found: C, 81.31; H, 7.20; N, 5.27.

EXAMPLE 10

3-Allyl-1,5-epoxy-1-phenyl-1,2,4,5-tetrahydro-3-benzazepin

A solution of methanesulfonyl chloride (1.95 ml, 25.19 mM) in CH$_2$Cl$_2$ (10 ml) was added dropwise to a solution of the diol (2.56 g, 10.0 mM), prepared as described in Example 6, and triethylamine (4.20 ml, 30.36 mM) in CH$_2$Cl$_2$ (35 ml) at 0° C. (ice bath). When the addition was complete, the mixture was stirred at 0° C. for 30 minutes and then poured onto ice containing 20 ml of 2N HCl solution. The organic layer was separated, washed with saturated NaCl solution, dried over anhydrous Na$_2$SO$_4$ and solvent removed in vacuo to give crude dimesylate.

The crude dimesylate was treated with allylamine (15.0 ml) and heated at 100° C. for 2.75 hours in a pressure bottle. The excess allylamine was evaporated and the residue was partitioned between CH$_2$Cl$_2$ and distilled water. The CH$_2$Cl$_2$ extract was dried over anhydrous Na$_2$SO$_4$ and concentrated in vacuo to give crude amino-mesylate.

The crude amino-mesylate was dissolved in DMF (25 ml), treated with finely powdered anhydrous K$_2$CO$_3$ (10.0 g, 0.0725M) and refluxed for two hours under nitrogen. The cooled mixture was diluted with ether and filtered. The filtered solution was then washed with several portions of distilled water and the combined aqueous washings re-extracted with ether. The combined ether extract was washed with saturated NaCl solution, dried over anhydrous K$_2$CO$_3$ and the ether removed in vacuo. The residue was purified by column chromatography on 75 g silica gel and eluted with EtOAc/hexane (1:10). The combined fractions were evaporated and the residue recrystallized from hexane to give the named compound (2.15 g, 78% yield) as white needles, mp 127°–128° C. NMR (CDCl$_3$) δ 2.65 ppm (AB doublet, 1H, J=11 Hz,

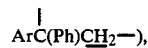

2.73 (s, 2H,

3.00 (d, 2H, J=6 Hz,

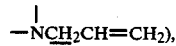

3.25 (AB doublet, 1H, J=11 Hz,

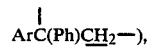

4.75–6.00 (m, 4H,

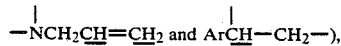

6.75–7.70 (m, 9H, aromatic H). MS: 277 (M+).
Theor. C$_{19}$H$_{19}$NO: C, 82.28; H, 6.90; N, 5.05. Found: C, 82.18; H, 6.95; N, 5.05.

EXAMPLE 11

3-[3-[[3-(1-Piperidinyl)methyl]methyl]phenoxy]-propyl]-1,5-epoxy-1-phenyl-1,2,4,5-tetrahydro-3-benzazepin dioxalate hemihydrate The dimesylate (3.20 g, 7.8 mM), prepared as described in Example 6, was heated with piperidinylmethylphenoxyamine (10 ml) at 130° C. for four hours. The crude reaction product was treated with Et$_2$O and filtered. The filtrate was concentrated in vacuo and purified via Kieselgel-60 (pH 7, 500 g) column chromatography and eluted with 3%-MeOH/CH$_2$Cl$_2$ to give the epoxy benzazepin (oil, 2.75 g, 76% yield). NMR(CDCl$_3$) δ 1.67 (m, 8H, piperidinyl-H$_{3,4,5}$, CH$_2$CH$_2$CH$_2$), 2.5 (m, 10H, piperidinyl-H$_{2,6}$, NCH$_2$), 3.43 (m, 4H, CH$_2$Ar, OCH$_2$), 5.27 (s, 1H, ArCHO), 6.4–7.7 (m, 13H, aromatic H).

A solution of this product (1.5 g, 230 mM) in MeOH/Et$_2$O (3/430 ml) was treated with equivalents of anhydrous oxalic acid in Et$_2$O to give the crude oxalate which was filtered. Recrystallization from EtOH/Et$_2$O afforded pure named compound (white solids, 1.14 g, 55% yield), mp 175°–177° C. NMR (DMSO-d$_6$) δ1.7 (brs, 8H, piperidinyl-H$_{3,4,5}$, CH$_2$—CH$_2$—CH$_2$), 5.37 (s, 1H, ArCHO), 7.17 (6m, 13H, aromatic H), 9.16 (bs, 2H, 2CO$_2$H), MS: 468 (M+).

Theor. C$_{35}$H$_{40}$N$_2$O$_{10}$.½H$_2$O: C, 63.91; H, 6.28; N, 4.26. Found: C, 63.77; H, 6.13; N, 4.47.

EXAMPLE 12

3-[2-[[[5-(Dimethylamino)methyl-2-furanyl]-methylthio]ethyl]-1,5-epoxy-1-phenyl-1,2,4,5-tetrahydro-3-benzazepin dioxalate hemihydrate To dimesylate (3.00 g, 0.0075M), prepared as described in Example 6, was added 2-[(5-dimethylaminomethyl-2-furanyl)-methylthio]ethylamine (3.90 g, 0.18M) prepared as described in Belgian Patent No. 857,388. The neat reaction mixture was heated under N$_2$ at 75° C. for three hours, dissolved in CH$_2$Cl$_2$ extracted with H$_2$O, and dried (Na$_2$SO$_4$). The solvent was evaporated in vacuo to a brown oil, to which was added dimethylformamide (25 ml) and K$_2$CO$_3$ (5.0 g). After heating at 160° C. for 2.5 hours under N$_2$, the reaction mixture was cooled, diluted with Et$_2$O and filtered. The solution was extracted with H$_2$O, saturated NaCl, and dried (K$_2$CO$_3$). The solvent was evaporated in vacuo to a brown oil which was chromatographed on silica gel (CH$_2$Cl$_2$/5% MeOH) to yield 1.52 g (47% yield) of epoxybenzazepin as a light brown oil. NMR (CDCl$_3$) δ 2.22 (s, 6H, N(CH$_3$)$_2$), 2.41–3.30 (m, 8H, CH$_2$(CH$_2$)NCH$_2$CH$_2$S), 3.50 (br s, 4H, —SCH$_2$, —CH$_2$N), 5.30 (t(br), 1H, ArCHO), 6.05 (m, 2H, furan-H), 6.88–7.55 (m, 9H, aromatic H); MS: 434 (M+).

To the epoxybenzazepin (2.5 g, 0.0057M) was added several portions of Et$_2$O. The ethereal portions were combined and filtered. To this solution was added a solution of oxalic acid (1.10 g, 0.012M) in Et$_2$O. The resulting precipitate was filtered and recrystallized several times from methanol-Et$_2$O to yield 680 mg (20% yield) of white crystalline named compound, mp 162°–164° C., NMR (DMSO-d$_6$) δ2.63 ppm (s, 6H, N(CH$_3$)$_2$), 2.63–3.41 (m, 8H, (CH$_2$)$_2$NCH$_2$CH$_2$S), 3.55 (s, 2H, —CH$_2$S), 4.25 (s, 2H, —CH$_2$N), 5.38 (t(br), 1H, ArCH—O), 6.22 (d, 1H, furan-H), 6.58 (d, 1H, furan-H), 6.80–7.62 (m, 9H, aromatic H), 8.42 (br, 4H, CO$_2$H). MS: 434 (M+).

Theor. $C_{30}H_{34}N_2O_{10}\cdot\frac{1}{4}H_2O$: C, 57.77; H, 5.66; N, 4.49. Found: C, 57.40; H, 5.52; N, 4.26.

EXAMPLE 13

3-Allyl-7-chloro-1,5-epoxy-1,2,4,5-tetrahydro-3-benzazepin oxalate.¼H₂O

4-Chloroanthranilic acid (34.32 g, 0.20M) in THF (100 ml) was added dropwise to a refluxing solution of furan (29.1 ml, 0.40M), i-AmONO (36.3 ml, 0.27M), and dry THF (150 ml) under nitrogen. After the addition was complete, refluxing was continued for one hour. The solvent was evaporated and the residue was treated with aqueous KOH, extracted into petroleum ether, washed twice with H₂O, saturated NaCl, dried (Na₂SO₄), and the solvent evaporated. The residue was chromatographed on neutral alumina (activity grade II), eluting first with hexane, then 1:3 CH₂Cl₂/hexane, then CH₂Cl₂. Fractions containing the desired product were combined and concentrated in vacuo to give an oil which was dissolved in petroleum ether. Crystallization, upon cooling, gave the olefin (13.0 g, 37% yield), mp 26°–28.5° C. NMR (CDCl₃) δ5.60 ppm [s, 2H,

2x(ArCHO)], 6.70–7.20 (m, 5H, —CH=CH—, aromatic H). MS: 180, 178 (M+), 115 (BP).

Ozone was passed into a solution of the olefin (12.6 g, 0.071M) in CH₂Cl₂ (150 ml) at −78° C. (dry ice-acetone bath) until a pale blue color was obtained. The solution was then transferred by cannulus to a solution of LiAlH₄ (6.94 g, 0.183M) in 150 ml dry THF at 0° C. (ice bath) under N₂. When the addition was complete, the mixture was allowed to warm to room temperature, then refluxed for one hour. It was cooled in an ice bath and treated successively with distilled H₂O (7.0 ml), 15% NaOH solution (7.0 ml) and H₂O (21.0 ml) in a dropwise manner. The resulting white suspension was filtered through Celite, washed with THF, and the washings dried (Na₂SO₄) and concentrated in vacuo. The product was recrystallized from EtOAc-hexane to give the diol (8.7 g, 68% yield), mp 119°–122° C. NMR (CDCl₃) δ3.0 ppm [s, 2H, (2x)—CH₂—OH], 3.60–4.15 [m, 4H, (2x)—CH₂—OH], 5.20 [s, 2H,

(2x) ArCHO], 7.00–7.35 (m, 3H, aromatic H). MS: 216, 214 (M+), 89 (BP).

A solution of methanesulfonyl chloride (7.74 ml, 0.100M) in CH₂Cl₂ (25 ml) was added dropwise to a solution of the diol (8.5 g, 0.04M) and triethylamine (16.5 ml, 0.12M) in CH₂Cl₂ (150 ml) at 0° C. After 20 minutes, the mixture was poured onto ice containing 2N HCl, and extracted with CH₂Cl₂. The extracts were washed with H₂O, dried (Na₂SO₄), and the solvent removed in vacuo. The crude dimesylate (2.1 g, 0.006M) was taken up in allylamine and heated in a pressure bottle at 100° C. for three hours. Upon cooling, the product was taken up in CH₂Cl₂ and evaporated. The residue was dissolved in CH₂Cl₂, washed with H₂O, dried (Na₂SO₄), and the solvent evaporated in vacuo. The residue was purified by column chromatography on silica gel, eluting with EtOAc/hexane (1:2) to give the epoxybenzazepin as a liquid. A solution of this product in ether was added dropwise to a solution of oxalic acid (6.05 g, 0.48M) in ether to give the named compound (1.3 g, 69% yield) as a white solid, mp 196°–198° C. NMR (DMSO-d₆) δ 2.65–3.20 ppm [m, 6H, —CH₂—N(CH₂)—CH₂], 5.10–5.25 [m, 5H,

(2x) ArCHO,

—CH=CH₂], 7.20–7.35 (m, 3H, aromatic H). MS: 237, 235 (M+), 83 (BP). IR (KBr): 1740 cm⁻¹ (CO₂H), 1650 cm⁻¹ (CO₂⁻).

For $C_{13}H_{14}NOCl\cdot C_2H_2O_4\cdot\frac{1}{4}H_2O$: Theor. C, 54.55; H, 5.04; N, 4.24. Found: C, 54.53; H, 4.96; N, 4.15.

EXAMPLE 14

7-Chloro-1,5-epoxy-1,2,4,5-tetrahydro-3-benzazepin oxalate.¼H₂O

Dimesylate, prepared as described in Example 13 from the diol (8.4 g, 0.039M) was dissolved in 3-amino-1-propanol (22 ml) and heated at 100° C. for two hours under nitrogen. The product was taken up in CH₂Cl₂, washed with H₂O, dried (Na₂SO₄) and evaporated in vacuo. The residue was purified by column chromatography on silica gel, eluting with ether, to give 3-hydroxypropyl-epoxybenzazepin (8.0 g, 81% yield) as an orange oil.

To a suspension of pyridinium chlorochromate (25 g, 0.116M) in CH₂Cl₂ (150 ml) was added a solution of the above product (7.45 g, 0.029M) in CH₂Cl₂ (150 ml) under nitrogen. After the reaction was allowed to proceed for two days, the reaction mixture was diluted with ether, and washed with 2N NaOH, saturated NaCl, dried (Na₂SO₄) and evaporated in vacuo to give the epoxybenzazepin (2 g, 35% yield) as a yellow oil. The crude product was purified first on preparative TLC plates developed in 10% MeOH/CH₂Cl₂, then by column chromatography on silica gel, eluting with 10% methanol/ether. The fractions containing the desired compound were combined and concentrated to give pure product. A solution of oxalic acid (1.1 g, 0.0085M) in ether was added dropwise to a solution of the pure product in ether to give the named compound as a white precipitate. The solid was collected and then recrystallized from methanol/acetone to give the named compound (1.87 g), which was suspended in ether, collected, and dried in vacuo, mp 197°–199° C. (dec). NMR (DMSO-d₆) δ 2.85–3.70 ppm (m, 4H, CH₂—N—CH₂), 5.35 [broad s, 2H, (2x), ArCHO], 7.45 (m, 3H, aromatic H), 8.35 [broad s, 3H, (2x) (COOH), NH]. MS: 195 (M+), 69 (BP). IR (KBr): 1750 cm⁻¹ (CO₂H), 1640 cm⁻¹ (CO₂⁻).

For $C_{10}H_{10}NOCl\cdot C_2H_2O_4\cdot\frac{1}{4}H_2O$: Theor. C, 49.67; H, 4.34; N, 4.83. Found: C, 49.90; H, 4.70; N, 4.55.

EXAMPLE 15

3-Benzyl-7-chloro-1,5-epoxy-1,2,4,5-tetrahydro-3-benzazepin oxalate hemihydrate

Dimesylate (12.0 g, 0.032M) was prepared as described in Example 13. The crude dimesylate was treated with benzylamine (20 ml) and heated at 100° C. under nitrogen for 45 minutes. The excess benzylamine was distilled in vacuo and the residue partitioned between CH₂Cl₂ and water. The CH₂Cl₂ extract was washed with H₂O, dried (Na₂SO₄), and evaporated.

The residue was purified by column chromatography on silica gel eluted with ether/hexane (1:4) to give the epoxybenzazepin as an oil. A solution of oxalic acid (4.8 g, 0.038M) in Et₂O was added dropwise to a solution of this product in Et₂O to give the titled compound (8.5 g, 69% yield) as a white precipitate, which was filtered and washed with ether, mp 183.5°–185° C. NMR (DMSO-d₆) δ 2.65–2.80 ppm (m, 4H, —C$\underline{H}$₂—N—C$\underline{H}$₂), 3.55 (s, 2H, N—C$\underline{H}$₂—Ph), 5.10 [broad t, 2H, J=2 Hz, (2x) ArC$\underline{H}$O], 6.80–7.35 (m, 8H, aromatic $\underline{H}$), 11.35 (broad s, 2$\underline{H}$, —COO$\underline{H}$). IR (KBr): 1740 cm⁻¹ (CO₂H), 1655 (CO₂—). MS: 285, 287 (M+).

For C₁₇H₁₆ClNO·C₂H₂O₄·½H₂O: Theor. C, 59.30; H, 4.98; N, 3.64. Found: C, 59.52; H, 4.82; N, 3.58.

EXAMPLE 16

3-Benzyl-7,8-dibenzyloxy-1,5-epoxy-1,2,4,5-tetrahydro-3-benzazepin

A mixture of catechol (11.0 g, 0.10M), benzylbromide (25.0 ml, 0.21M) and finely powdered anhydrous K₂CO₃ (44.2 g, 0.32M) in DMF (60 ml) was stirred at room temperature under N₂ for 72 hours. The mixture was then diluted with Et₂O and filtered. The ether solution was washed with three portions of distilled water, one portion of saturated NaCl solution, dried (K₂CO₃) and concentrated in vacuo. The residue was recrystallized from hexane to give dibenzyloxybenzene (27.04 g, 93% yield) as white crystals, mp 58°–59° C. (literature: Page et al., *J. Org. Chem.* 27, 218 (1962), mp 58°–59° C.).

A solution of this product (14.38 g, 0.0496M) in refluxing 95% ethanol (80 ml) was treated with iodine (38.97 g, 0.1535M) and yellow mercuric oxide (31.66 g, 0.1462M). The iodine and mercuric oxide were added alternately in small portions over a period of three hours. After the addition was complete, reflux was continued for one hour. The cooled mixture was filtered through Celite and concentrated. The residue was taken up in hot hexane and again filtered and evaporated. The residue was then filtered through Al₂O₃ (neutral, activity grade I; CH₂Cl₂/hexane, 1:2). The fractions containing the desired product was combined and evaporated. The residue was recrystallized from MeOH to give the iodo compound (16.5 g, 80% yield) as white crystals, mp 64°–65° C. (literature: Musso et al., *Chem. Ber.* 100(9), 2854 (1967) mp 65°–67° C.).

A solution of this product (16.5 g, 39.7 mM) and sodium acetate (6.69 g, 81.6M) in acetic acid (165 ml) was treated with bromine (4.4 ml, 85.9 mM) and stirred at 40° C. for one hour. The mixture was diluted with water and treated with sodium bisulfite to discharge the excess bromine. The white solid was filtered, washed with water and dried in vacuo over P₂O₅ to give crude 4,5-dibenzyloxy-2-iodobromobenzene (18.8 g, 96% yield). The crude product was recrystallized from EtOH to give pure product (17.2 g) as white plates, mp 121°–122° C. NMR (CDCl₃) δ 5.07 ppm [s, 4H, (2x) OC$\underline{H}$₂Ph], 7.13 (s, 1H, ArH₆), 7.33 [s, 11H, ArH₃ and (2x) OCH₂C₆$\underline{H}$₅]. MS: 494, 496 (M+), 91 (BP, C₇$\underline{H}$₇+).

A solution of this product (12.3 g, 24.85 mM) in a mixture of furan (100 ml) and anhydrous ether (100 ml) at −78° C. (dry ice/acetone bath) under nitrogen was treated dropwise via syringe with n-BuLi (12.0 ml, 2.30M in hexane, 27.6 mM) over a period of 15 minutes. After 2.5 hours at −78° C., the mixture was allowed to warm to room temperature and stirred for an additional 1.5 hours. The mixture was then poured onto saturated NH₄Cl solution and extracted with CH₂Cl₂. The combined extracts were dried over anhydrous Na₂SO₄ and evaporated. The residue was recrystallized from EtOAc/hexane to give pure olefin (5.50 g, 62% yield) as white crystals, mp 97°–98° C. NMR (CDCl₃) δ 5.10 ppm [s, 4H, (2x) OC$\underline{H}$₂Ph], 5.60 [s, 2H,

(2x) ArC$\underline{H}$O—], 6.97 (s, 4H, (2x) Ar$\underline{H}$ and C$\underline{H}$=C$\underline{H}$), 7.37 [s, 10H, (2x) OCH₂C₆$\underline{H}$₅]. MS: 356 (M+), 91 (BP, C₇H₇+).

Ozone was passed into a solution of the olefin (8.12 g, 22.8 mM) in CH₂Cl₂ (125 ml) at −78° C. (dry ice/acetone bath) until a pale blue color was obtained. Nitrogen was then passed into the solution to discharge the blue color and the resulting solution transferred via cannulus to a suspension of LiAlH₄ (2.50 g, 65.8 mM) in dry THF (150 ml) at 0° C. (ice bath) under a nitrogen atmosphere. The resulting mixture was stirred at 0° C. for 30 minutes, room temperature for 30 minutes, and then refluxed for one hour. The mixture was then cooled in an ice bath and treated successively with distilled water (2.5 ml), 15% NaOH solution (2.5 ml) and water (7.5 ml) in a dropwise manner. The resulting white suspension was filtered through Celite, the filtrate washed thoroughly with THF, and the combined washings concentrated in vacuo. The residue was recrystallized from EtOAc/hexane to give the diol (6.28 g, 70% yield) as white crystals, mp 131°–132° C. NMR (CDCl₃) δ 3.10–4.10 ppm [m, 6H, (2x) —C$\underline{H}$₂OH], 5.07 [s, 4H, (2x) OC$\underline{H}$₂Ph], 5.15 [broad s, 2H,

(2x) ArC$\underline{H}$O—], 6.72 [s, 2H, (2x) Ar$\underline{H}$], 7.33 [m, 10H, (2x) OCH₂C₆$\underline{H}$₅]. MS: 392 (M+).

A solution of methanesulfonyl chloride (3.70 ml, 47.8 mM) in CH₂Cl₂ (25 ml) was added dropwise to a solution of the diol (7.40 g, 18.9 mM) and triethylamine (9.0 ml, 65.0 mM) in CH₂Cl₂ (100 ml) at 0° C. (ice bath). After 20 minutes, the mixture was poured onto ice containing 35 ml of 2N HCl solution and extracted with CH₂Cl₂. The CH₂Cl₂ extracts were washed with water, dried over anhydrous Na₂SO₄ and solvent removed in vacuo to give crude dimesylate.

The crude dimesylate was treated with freshly distilled benzylamine (20 ml) and heated at 100° C. under nitrogen for 1.5 hours. The excess benzylamine was distilled in vacuo and the residue partitioned between CH₂Cl₂ and distilled water.

The CH₂Cl₂ extract was washed with H₂O, dried over anhydrous Na₂SO₄ and evaporated. The residue was purified by column chromatography on SilicAR 7 (280 g) eluted with EtOAc/hexane (1:6) to give pure titled compound (7.42 g, 85% yield from the diol) as white crystals, mp 100°–101° C. after crystallization from hexane. NMR (CDCl₃) δ 2.62 ppm (d, 4H, J=2 Hz, C$\underline{H}$₂—N—C$\underline{H}$₂), 3.43 (s, 2H, —NC$\underline{H}$₂Ph), 4.93 [broad t, 2H, (2x) ArC$\underline{H}$O], 5.10 [s, 4H, (2x) OC$\underline{H}$₂Ph], 6.8–7.6 (m, 17H, aromatic $\underline{H}$). MS: 463 (M+).

Theor. C₃₁H₂₉NO₃: C, 80.32; H, 6.31; N, 3.02. Found: C, 80.10; H, 6.47; N, 2.99.

EXAMPLE 17

7,8-Dihydroxy-1,5-epoxy-1,2,4,5-tetrahydro-3-benzazepin oxalate

A solution of the product prepared in Example 16 (3.58 g, 0.008M) in EtOH (150 ml) and AcOH (15 ml), was hydrogenated (1.80 g, 10% Pd-C) in a Parr apparatus at an initial pressure of 40 psi for 2.5 hours. The resulting solution was filtered through Celite, washed well with methanol, and evaporated to give the epoxybenzazepin. To a solution of this compound in methanol was added oxalic acid (1.94 g) in methanol. The solution was concentrated and then diluted with ether to give a yellow precipitate of the named compound, which was collected and washed with ether. The solid was resuspended in ether, collected, and dried in vacuo to give pure product (2.0 g, 92% yield), mp 210°–212° C. (dec). NMR (DMSO-$d_6$) δ 1.90–3.55 ppm (m, 4H, —CH$_2$—N—CH$_2$), 5.10 [s, 2H, (2x) ArCHO], 6.75 (s, 2H, aromatic H̲), 7.25 [broad s, 5H, (2x) OH̲, —NH, (2x) CO$_2$H̲). MS: 193 (M+), 136 (BP). IR (KBr): 1720 cm$^{-1}$ CO$_2$H̲), 1600 cm$^{-1}$ (CO$_2^-$).

Theor. C$_{10}$H$_{11}$NO$_3$.C$_2$H$_2$O$_4$: C, 50.89; H, 4.63; N, 4.95. Found: C, 50.52; H, 5.16; N, 4.62.

EXAMPLE 18

3-Benzyl-1,5-epoxy-1,2,4,5-tetrahydro-3-benzazepin oxalate

2-Bromofluorobenzene (22.5 ml, 0.206 M) in THF (150 ml) was added dropwise over one hour to a refluxing mixture of furan (29 ml, 0.400M) and magnesium turnings (5.4 g, 0.222M) in dry THF (150 ml) under nitrogen. After the addition was complete, refluxing was continued for one hour. The cooled mixture was then poured onto saturated NH$_4$Cl solution, the organic layer separated and the aqueous layer re-extracted with ether. The combined organic extracts were washed with H$_2$O, dried (Na$_2$SO$_4$), and concentraed in vacuo. The residue was purified by column chromatography on neutral alumina (activity grade II) and eluted with CH$_2$Cl$_2$/hexane (1:2). Crystallization from petroleum ether gave 12.0 g (40.5% yield) of olefin as white crystals, mp 52°–54° C. NMR (CDCl$_3$) δ 5.65 ppm [s, 2H, (2x) ArCHO—], 6.80–7.40 (m, 6H, —CH=CH— and aromatic H̲). MS: 144 (M+).

Ozone was passed into a solution of this product (9.95 g, 0.069 M) in CH$_2$Cl$_2$ (100 ml) at −78° C. (dry ice/acetone bath) until a pale blue color was obtained. Nitrogen was then passed into the solution to discharge the blue color. The solution was then transferred by cannulus to a solution of LiAlH$_4$ (6.56 g, 0.17M) in 150 ml dry THF at 0° C. (ice bath) under N$_2$. When the addition was complete, the mixture was allowed to warm to room temperature, stirred for 30 minutes, then refluxed for 30 minutes. It was cooled in a ice bath and treated successively with distilled H$_2$O (6.6 ml), 15% NaOH solution (6.6 ml), and H$_2$O (19.8 ml) in a dropwise manner. The resulting white suspension was filtered through Celite, washed with THF, and the washings were dried (Na$_2$SO$_4$) and concentrated in vacuo. The white crystals were collected with hexane to give the diol (8.17 g, 66% yield), mp 109°–111° C. NMR (CDCl$_3$) δ 3.00 ppm [s, 2H, (2x) CH$_2$—OH], 3.95 [m, 4H, (2x) CH̲$_2$—OH], 5.35 [s, 2H, (2x) ArCHO], 7.25 (m, 4H, aromatic H̲). MS: 180 (M+).

A solution of methanesulfonyl chloride (12.1 ml, 0.156M) in CH$_2$Cl$_2$ (25 ml) was added dropwise to a solution of the diol (9.33 g, 0.052M) and triethylamine (26.6 ml, 0.192M) in CH$_2$Cl$_2$ (150 ml) at 0° C. After 20 minutes, the mixture was poured onto ice containing 2N HCl solution (75 ml) and extracted with CH$_2$Cl$_2$. The extracts were washed with water, dried (Na$_2$SO$_4$) and the solvent removed in vacuo. The crude dimesylate was treated with freshly distilled benzylamine (20 ml) and heated at 100° C. under nitrogen for 45 minutes. The excess benzylamine was distilled in vacuo and the residue partitioned between CH$_2$Cl$_2$ and water. The CH$_2$Cl$_2$ extract was washed with H$_2$O, dried (Na$_2$SO$_4$), and evaporated. The residue was purified by column chromatography on 400 g of SilicAR CC-7 eluted with ether/hexane (1:5) to give the epoxybenzazepin (10.1 g, 78% yield) as a yellow oil. A solution of oxalic acid (0.96 g, 0.008M) in Et$_2$O was added dropwise to a solution of this product (1.60 g, 0.006M) in Et$_2$O to give the titled compound (1.93 g, 89% yield) as a white precipitate, which was filtered and washed with ether, mp 172°–174° C. NMR (DMSO-$d_6$) δ 2.85 ppm (d, 4H, J=2 Hz,

—CH$_2$—N—CH$_2$—), 3.65 (s, 2H

—N—CH$_2$—Ph), 4.90 [s, 2H, (2x) COOH̲], 5.10 (broad t, 2H, J=2 Hz, (2x) ArCHO—), 6.90–7.35 (m, 9H, aromatic H̲). IR (KBr): 3420 cm$^{-1}$ (OH̲), 1720 cm$^{-1}$ (CO$_2$H), 1600 cm$^{-1}$ (CO$_2^\ominus$). MS: 251 (M+).

Theor. C$_{17}$H$_{17}$NO.(COCH)$_2$: C, 66.85; H, 5.61; N, 4.10. Found: C, 66.98; H, 5.59; N, 4.00.

EXAMPLE 19

1,5-Epoxy-1,2,4,5-tetrahydro-3-benzazepin oxalate

A suspension of 10% Pd-C (0.32 g) in a solution of the product of Example 18 (3.20 g, 0.009M) in methanol (100 ml) was hydrogenated in a Parr apparatus at an initial pressure of 25 psi. After four hours, the suspension was filtered through Celite, the solvent evaporated and the residue was triturated with ether to give 1.60 g (68% yield) of the named compound as a white crystalline solid, mp 219°–222° C. NMR (DMSO-$d_6$) δ 2.80–3.60 ppm (m, 4H, CH$_2$—NH—CH$_2$), 5.15–5.35 [broad s, 2H, (2x) ArCHO], 7.15–7.45 (broad s, 4H, aromatic H̲), 7.80–8.20 [broad s, 4H, —NH, (2x)

COOH, H$_2$O]. IR (KBr): 1750 cm$^{-1}$ (CO$_2$H), 1675 (CO$_2$⊖). MS: 161 (M+), 104 (BP).

Theor. C$_{10}$H$_{11}$NO.C$_2$H$_2$O$_4$: C, 57.37; H, 5.22; N, 5.58. Found: C, 57.05; H, 5.24; N, 5.17.

EXAMPLE 20

1,5-Epoxy-3-propyl-1,2,4,5-tetrahydro-3-benzazepin oxalate monohydrate

The product prepared in Example 19 (3.85 g, 0.15M) was made basic with NaOH, partitioned between H$_2$O and CH$_2$Cl$_2$, and the organic layer dried (Na$_2$SO$_4$) and evaporated to give the 3-H-epoxybenzazepin (2.50 g, 0.015M). This compound was treated with propionic anhydride (10 ml) and allowed to stir for two hours. Excess propionic anhydride was removed in vacuo to give 3-propoxy-epoxybenzazepin as a white solid (3.3 g, 98% yield).

To a cold (0° C.) suspension of LiAlH$_4$ (1.7 g, 0.046M) in THF (150 ml) was added this product (3.3 g, 0.015M), and the mixture refluxed for three hours. The mixture was then allowed to cool, treated successively with H$_2$O (1.7 ml), 15% NaOH (1.7 ml) and H$_2$O (5.1 ml), filtered through Celite and evaporated to give 3-propyl-epoxybenzazepin as an oil. A solution of oxalic acid (2.3 g, 0.018M) in ether was added dropwise to a solution of this compound in ether to give the named compound (3.7 g, 83% yield). The solid was collected and recrystallized from MeOH/acetone to give pure product as white crystals, mp 186°–188° C. NMR (DMSO-d$_6$) δ 0.50–0.85 ppm (m, 3H, —CH$_2$CH$_3$), 1.20–1.50 (m, 2H, —CH$_2$CH$_3$), 2.45–2.75 (m, 2H, N—CH$_2$CH$_2$), 3.10 (m, 4H, CH$_2$—N—CH$_2$), 5.25 [m, 2H, (2x) ArCHO], 7.35 (s, 4H, aromatic H), 9.25 [m, 2H, (2x) CO$_2$H]. MS: 203 (M+), 84 (BP). IR (KBr): 3440 cm$^{-1}$ (OH), 1725 cm$^{-1}$ (CO$_2$H), 1590 cm$^{-1}$ (CO$_2$-).

For C$_{13}$H$_{17}$NO.C$_2$H$_2$O$_4$.H$_2$O: Theor. C, 57.87; H, 6.80; N, 4.50. Found: C, 56.91; H, 5.97; N, 4.03.

EXAMPLE 21

1,5-Epoxy-3-ethyl-1,2,4,5-tetrahydro-3-benzazepin oxalate

A solution of the compound prepared in Example 18 (6.1 g, 0.018M) in methanol (300 ml) was hydrogenated (0.61 g, 10% Pd-C) in a Parr apparatus at an initial pressure of 30 psi for 3.5 hours. The resulting solution of the product in methanol was made basic with aqueous NaOH, filtered through Celite and evaporated. The residue was partitioned between H$_2$O and CH$_2$Cl$_2$; the organic layer was dried (Na$_2$SO$_4$) to give 3-H-epoxybenzazepin (1.95 g, 68% yield). This compound was treated with acetic anhydride (6 ml) and allowed to stir for two hours. Excess acetic anhydride was removed in vacuo to give 3-acetylepoxybenzazepin as a white solid (2.2 g), mp 126°–128° C. NMR (CDCl$_3$) δ 1.80 ppm (s, 3H, —CH$_3$), 3.10–4.45 (m, 4H, —CH$_2$—N—CH$_2$), 5.20 [m, 2H, (2x), ArCHO], 7.30 (s, 4H, aromatic H). MS: 203 (M+).

To a cold (0° C.) suspension of LiAlH$_4$ (1.7 g, 0.045M) in THF (200 ml) was added a solution of this product (3.0 g, 0.015M) in THF (100 ml) and the resulting mixture refluxed for three hours. The reaction mixture was then allowed to cool, treated successively with H$_2$O (1.7 ml), 15% NaOH (1.7 ml) and H$_2$O (5.1 ml), filtered through Celite, and evaporated to give 3-ethyl-epoxybenzazepin as an oil. A solution of oxalic acid (2.1 g, 0.017M) in Et$_2$O was added dropwise to a solution of this product in Et$_2$O to give the titled compound (4.15 g, 99% yield) as a white precipitate. The solid was collected and recrystallized from MeOH/acetone to give pure product (2.96 g) as white crystals, mp 185°–187° C. NMR (DMSO-d$_6$) δ 0.80–1.15 ppm (t, 3H, —CH$_2$—CH$_3$), 2.60–3.30 [m, 6H, —CH$_2$—N(CH$_2$)—CH$_2$], 5.25 [s, 2H, (2x) ArCHO]. 7.30 (s, 4H, aromatic H), 11.00 [s, 2H, (2x) CO$_2$H]. IR (KBr): 3400 cm$^{-1}$ (OH), 1750 cm$^{-1}$ (CO$_2$H), 1640 (CO$_2$-). MS: 189 (M+), 71 (BP).

Theor. C$_{12}$H$_{15}$NO.C$_2$H$_2$O$_4$: C, 60.21; H, 6.14; N, 5.02. Found: C, 59.96; H, 6.01; N, 5.03.

EXAMPLE 22

1,5-Epoxy-3-[N-(3-morpholinopropyl)]-1,2,4,5-tetrahydro-3-benzazepin dioxalate

Dimesylate (12.1 g, 0.036M), prepared as described in Example 18, was heated with N-(3-aminopropyl)morpholine (15 ml) at 135° C. for one hour under N$_2$. Upon cooling, excess N-(3-aminopropyl)morpholine was removed in vacuo and the product was taken up in CH$_2$Cl$_2$, washed twice with H$_2$O, saturated with NaCl, dried (Na$_2$SO$_4$), and evaporated. The residue was purified by column chromatography on silica gel, eluting with 5% MeOH/CH$_2$Cl$_2$. Fractions containing the desired compound were combined and concentrated to give the epoxybenzazepin. A solution of oxalic acid (5.0 g, 0.04M) in ether was added dropwise to a solution of the product in ether to give the named compound (7.3 g, 43% yield) as an off-white precipitate, mp 185°–187° C. (dec). NMR (DMSO-d$_6$) δ 1.6 ppm (m, 2H, N—CH$_2$—CH$_2$—CH$_2$—N), 2.5–2.95 [m, 12H, (2x), H$_2$C—N(CH$_2$)CH$_2$], 3.50–3.80 (m, 4H, CH$_2$—OCH$_2$), 5.10 [m, 2H, (2x) ArCHO], 7.20 (s, 4H, aromatic H), 10.00 [broad s, 4H, (4x) CO$_2$H]. MS: (M+) −18 (270), 69 (BP). IR (KBr): 3400 cm$^{-1}$ (OH), 1700 cm$^{-1}$ (CO$_2$H), 1620 cm$^{-1}$ (CO$_2$⊖).

Theor. C$_{17}$H$_{24}$N$_2$O$_2$.C$_4$H$_4$O$_8$: C, 53.84; H, 6.02; N, 5.98. Found: C, 54.07; H, 6.05; N, 5.82.

EXAMPLE 23

1,5-Epoxy-3-[N-(2-morpholinoethyl)]-1,2,4,5-tetrahydro-3-benzazepin dioxalate

Dimesylate (3.92 g, 0.012M), prepared as described in Example 18, was heated with N-(2-aminoethyl)morpholine (8 ml) at 130° C. for three hours under N$_2$. Upon cooling, excess N-(2-aminoethyl)morpholine was removed in vacuo and the product was taken up in CH$_2$Cl$_2$, washed twice with H$_2$O, saturated NaCl, dried (Na$_2$SO$_4$), and evaporated. The residue was purified by column chromatography on silica gel, eluting with 5% MeOH/CH$_2$Cl$_2$, then 10% MeOH/CH$_2$Cl$_2$. Fractions containing the desired compound were combined and concentrated to give the epoxybenzazepin. A solution of oxalic acid (1.6 g, 0.013M) in ether was added dropwise to a solution of this product in ether to give the named compound (3.00 g, 57% yield), which was recrystallized from MeOH/CH$_3$COCH$_3$ as a white powder, mp 201°–202° C. (dec). NMR (DMSO-d$_6$) δ 2.30–2.90 ppm [m, 12H, (6x), H$_2$C—N—], 3.30–3.65 (m, 4H, —CH$_2$OCH$_2$—), 5.10 [s, 2H, (2x) ArCHO], 7.15 (s, 4H, aromatic H). MS: 274 (M+), 174 (BP); IR (KBr): 3400 cm$^{-1}$ (OH), 1720 cm$^{-1}$ (CO$_2$H), 1600 cm$^{-1}$ (CO$_2$-).

Theor. C$_{16}$H$_{22}$N$_2$O$_2$.C$_4$H$_4$O$_8$: C, 52.86; H, 5.77; N, 6.16. Found: C, 52.76; H, 5.96; N, 5.97.

EXAMPLE 24

3-Allyl-1,5-epoxy-1,2,4,5-tetrahydro-3-benzazepin oxalate.¼H₂O

The diol (2.20 g, 0.012M) was converted to dimesylate as described in Example 18. Crude dimesylate was taken up in allylamine (15 ml) and heated at 100° C. in a pressure bottle for three hours. The product was taken up in CH₂Cl₂ and washed with H₂O, dried (Na₂SO₄), and the solvent evaporated in vacuo. The residue was purified by column chromatography on silica gel and was eluted with EtOAc:hexane (1:2). Fractions containing the desired product were combined and concentrated to give the epoxybenzazepin as a liquid. A solution of this product in ether was added dropwise to a solution of oxalic acid (1.8 g, 0.0144M) in ether to give the titled compound (3.3 g, 94% yield). The crude product was recrystallized from isopropanol to give pure product (2.4 g, 69% yield), mp 169°–172° C. NMR (DMSO-d₆) δ 2.80–3.35 ppm (m, 6H, —CH₂—N—CH₂ and —CH₂—CH=CH₂), 5.00–5.30 [m, 5H, (2x) Ar-CHO, —CH=CH₂), 7.15–7.35 (broad s, 4H, aromatic H), 12.35–12.50 [broad s, 2H, (2x) CO₂H]. IR (KBr): 3440 cm⁻¹ (OH), 1745 cm⁻¹ (CO₂H), 1645 (CO₂⊖). MS: 201 (M+), 83 (BP).

For C₁₃H₁₅NO.C₂H₂O₄.¼H₂O: Theor. C, 60.91; H, 5.96; N, 4.74. Found: C, 61.01; H, 5.92; N, 4.64.

EXAMPLE 25

1,5-Epoxy-3-[(4'-methoxy)phenyl]-1,2,4,5-tetrahydro-3-benzazepin

Dimesylate (4.13 g, 0.012M), prepared as described in Example 18, was treated with p-anisidine (3 g, 0.024M) and heated for one hour at 95° C. under N₂. The crude product was cooled, taken up in CH₂Cl₂, washed twice with H₂O, dried (Na₂SO₄), and the solvent removed in vacuo. The residue was purified by column chromatography, eluting with 10% ether/hexane. Fractions containing the desired compound were combined and concentrated to give the named compound, which was recrystallized from Et₂O (0.76 g, 24% yield), mp 105°–106° C.; NMR (CDCl₃) δ 3.45 ppm (m, 4H, CH₂—N—CH₂), 3.70 (s, 3H, OCH₃), 5.30 (m, 2H (2x) ArCHO), 6.70 (m, 4H, aromatic H'), 7.30 (s, 4H, aromatic H); MS: 267 (M+).

Theor. C₁₇H₁₇NO₂: C, 76.38; H, 6.41; N, 5.24. Found: C, 76.42; H, 6.28; N, 5.21.

EXAMPLE 26

1,5-Epoxy-3-(3-hydroxypropyl)-1,2,4,5-tetrahydro-3-benzazepin

Dimesylate was prepared as described in Example 18 from the diol (2.30 g, 12.8 mM). The crude dimesylate was treated with 3-amino-1-propanol (8.0 ml, 0.105M) and heated at 100° C. for one hour under nitrogen. The excess 3-amino-1-propanol was distilled in vacuo and the residue partitioned between CH₂Cl₂ and distilled water. The CH₂Cl₂ extract was then dried (Na₂SO₄) and concentrated in vacuo. The residue was purified by column chromatography on SilicAR CC-7 (50 g, eluted with Et₂O) to give pure named compound (2.15 g, 77% yield) as white crystals, mp 58°–59° C., after recrystallization from hexane. NMR (CDCl₃) δ 1.50 ppm (quintet, 2H, J=5 Hz, —NCH₂CH₂CH₂OH), 2.40–3.10 (m, 6H, (CH₂)₂—N—CH₂—), 3.43 (t, 3H, J=5 Hz, —CH₂OH), 5.10 (t, 2H, J=2 Hz,

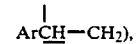

7.27 (s, 4H, aromatic H). IR (KBr): 3380 cm⁻¹ (broad, —OH. MS: 219 (M+).

Theor. C₁₃H₁₇NO₂: C, 71.21; H, 7.81; N, 6.39. Found: C, 71.15; H, 7.76; N, 6.42.

EXAMPLE 27

3-Benzyl-7,8-dimethoxy-1-(1,3-dioxolan-2-yl)-1,5-epoxy-1,2,4,5-tetrahydro-3-benzazepin.¼H₂O A solution of 6-nitroveratric acid (10.3 g, 45.37 mM) in absolute EtOH (180 ml) was treated with PtO₂ (305 mg) and shaken in a Parr apparatus at an initial pressure of 45 psi. After three hours, a white precipitate formed, the catalyst was filtered off through Celite and washed thoroughly with acetone to dissolve the white solid. The solvents were removed in vacuo, the residue was taken up in the minimum amount of boiling EtOH and treated with concentrated HCl (4.5 ml). The solution was cooled and diluted with Et₂O. The white precipitate was filtered and washed thoroughly with Et₂O to give the ammonium derivative (9.50 g, 90% yield) as white crystals.

i-Amylnitrite (25.0 ml, 0.186M) was added dropwise to a suspension of this product (22.6 g, 0.097M) in a solution of concentrated HCl (2.0 ml, 0.024M) in absolute EtOH (700 ml) while the temperature was maintained below 10° C. with an ice bath. After one hour at 0° C., dry Et₂O (1.2 liters) was added and the mixture stirred at 0° C. for one hour. The pale yellow precipitate was collected by suction and washed thoroughly with dry Et₂O to give the azide derivative as pale yellow crystals (22.5 g, 95% yield), mp 148° C. (dec.). NMR (DMSO-d₆) δ 4.00 ppm (s, 3H, —OCH₃), 4.13 (s, 3H, —OCH₃), 6.47 (s, 3H, —CO₂H and H₂O), 7.77 (s, 1H, ArH), 8.90 (s, 1H, ArH). IR (nujol): 2250 cm⁻¹ (—N≡N).

A suspension of the azide (10.0 g, 0.04M) in a solution of 2-(1,3-dioxolanyl) furan (11.2 g, 0.08M), propylene oxide (25 ml) and 1,4-dichlorobutane (75 ml) was heated at 135° C. and the temperature slowly raised to 145° C. over a period of 1.5 hours. After an additional hour at 145° C., all solid had gone into solution and gas evolution had ceased. The solvents were removed by vacuum distillation (~2 mm, bath temperature 75° C.). The residue was taken up in CH₂Cl₂ (5–10 ml), diluted with Et₂O (200 ml) and filtered through Celite. The filtered solution was washed with two portions of 2N NaOH solution. The base wash was re-extracted with Et₂O and the combined Et₂O extracts washed with saturated NaCl, dried over K₂CO₃ and evaporated. The residue was combined with that of an identical experiment starting with 14.8 g of the olefin. The combined products were purified by column chromatography on SilicAR (420 g) eluting with Et₂O/CH₂Cl₂/hexane (1:10:10), changing over to Et₂O/CH₂Cl₂/hexane (1:10:5), and finally Et₂O/CH₂Cl₂ (1:10). The product was crystallized from hexane to give the olefin (12.25 g, 44% yield) as pink crystals, mp 135°–136° C. NMR (CDCl₃) δ 3.83 ppm, (s, 3H, OCH₃), 3.85 (s, 3H, OCH₃), 4.12 (m, 4H, —OCH₂CH₂O—), 5.60 (s, 1H,

5.66 (d, 1H, J=1.5 Hz,

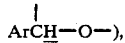

6.90–7.20 (m, 4H, aromatic and —CH=CH—).

Ozone was passed into a solution of the olefin (12.13 g, 0.044M) in a mixture of CH$_2$Cl$_2$ (60 ml) and MeOH (240 ml) at −78° C. (dry ice/acetone bath) until a pale blue-green color was obtained. Nitrogen was then added into the solution to discharge the color and Me$_2$S (20.0 ml, 0.277M) was added. After stirring at −78° C. for 30 minutes, 0° C. (ice bath) for 30 minutes, and room temperature for 30 minutes, the solvents were removed in vacuo. Benzene (100 ml) was added to the residue and again evaporated to dryness.

The residue was taken up in dry THF (150 ml) and added dropwise to a suspension of LiAlH$_4$ (5.12 g, 0.135M) in dry THF (150 ml). When the addition was complete, the mixture was refluxed for 45 minutes, cooled in an ice bath and treated successively with distilled water (5 ml), 15% NaOH solution (5 ml) and water (15 ml) in a dropwise manner. The resulting white suspension was filtered through Celite, the filtrate washed thoroughly with THF, and the combined washings concentrated in vacuo. The residue was crystallized from Et$_2$O to give the diol (10.43 g, 76% yield) as white crystals, mp 107°–108° C. NMR (CDCl$_3$) δ 3.20 ppm (broad s, 2H, (2x), OH), 3.70–4.20 (m, 14H, (2x) OCH$_3$, (2x) CH$_2$OH and OCH$_2$CH$_2$O), 5.00 (s, 1H,

5.33 (broad t, 1H, J=3 Hz,

6.67 (s, 1H, ArH), 6.76 (s, 1H, ArH).

A solution of methanesulfonyl chloride (6.5 ml, 83.98 mM) in CH$_2$Cl$_2$ (25 ml) was added dropwise to a solution of the diol (10.43 g, 33.43 mM) and triethylamine (13.8 ml, 99.79 mM) in CH$_2$Cl$_2$ (100 ml) at 0° C. (ice bath). When the addition was complete, the mixture was stirred at 0° C. for 30 minutes and then poured onto ice containing 60 ml of 2N HCl solution. The organic layer was separated, washed with distilled H$_2$O, dried over anhydrous Na$_2$SO$_4$ and the solvent removed in vacuo to give crude dimesylate.

The crude dimesylate was treated with freshly distilled benzylamine (20.0 ml, 0.183M) and heated at 100° C. for three hours under nitrogen. The excess benzylamine was distilled in vacuo and the residue partitioned between CH$_2$Cl$_2$ and distilled H$_2$O. The CH$_2$Cl$_2$ extract was then dried over anhydrous Na$_2$SO$_4$ and concentrated in vacuo.

The residue was dissolved in DMF (100 ml), treated with powdered anhydrous K$_2$CO$_3$ (40.1 g, 0.29M) and refluxed for two hours under nitrogen. The cooled mixture was diluted with ether and filtered. The filtered solution was then washed with several portions of distilled H$_2$O and the combined aqueous washings re-extracted with Et$_2$O. The combined Et$_2$O extract was washed with saturated NaCl solution, dried over anhydrous K$_2$CO$_3$ and the solvent removed in vacuo. The residue was purified by column chromatography on 400 g of SilicAR eluted with EtOAc-hexane (1:2) to give pure titled compound (10.63 g, 83% yield from the diol) as white crystals, mp 123°–124.5° C. after crystallization from hexane. NMR (CDCl$_3$) δ 2.67 ppm (m, 4H,

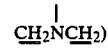

3.48 (s, 2H, PhCH$_2$N<), 3.87 (s, 3H, OCH$_3$), 3.90 (s, 3H, OCH$_3$), 3.98 (m, 4H, OCH$_2$CH$_2$O), 5.13 (m, 2H,

ArCH—CH$_2$N and OCHO), 6.70–7.30 (m, 7H, aromatic); MS: 383 (M+), 191 (BP).
Theor. C$_{22}$H$_{25}$NO$_5$.¼H$_2$O: C, 68.11; H, 6.62; N, 3.61.
Found: C, 68.02; H, 6.33; N, 3.61.

EXAMPLE 28

7,8-Dimethoxy-1-(1,3-dioxolan-2-yl)-1,5-epoxy-1,2,4,5-tetrahydro-3-benzazepin.⅜H$_2$O A suspension of 10% Pd-C (1.20 g) in a solution of the product of Example 27 (4.50 g, 11.75 mM) and glacial acetic acid (14.0 ml) in absolute ethanol (140 ml) was hydrogenated in a Parr apparatus at an initial pressure of 25 psi. After 2.5 hours, the mixture was filtered through Celite and the solvents removed in vacuo. The residue was taken up in CH$_2$Cl$_2$ and stirred with saturated NaHCO$_3$ solution (5 ml). The mixture was then treated with anhydrous K$_2$CO$_3$ until all of the aqueous phase had been absorbed. The solid was filtered and washed thoroughly with CH$_2$Cl$_2$. Evaporation of the CH$_2$Cl$_2$ solution gave crude product (2.64 g, 77% yield) as a colorless oil. Crystallization from Et$_2$O gave pure titled compound (2.29 g, 66.5% yield) as white crystals, mp 107°–109° C. NMR (CDCl$_3$) δ 1.72 ppm (broad s, 1H, NH), 2.30–3.50 (m, 4H, —CH$_2$NHCH$_2$—), 3.90 (s, 6H, (2x) OCH$_3$), 4.00 (m, 4H, —OCH$_2$CH$_2$O—), 5.08 (s, 2H, ArCHO— and —OCHO—), 6.80 (s, 1H, ArH), 7.00 (s, 1H, ArH). IR (KBr): 3470 (broad), 3340 (sharp), 1610 cm$^{-1}$ (NH). MS: 293 (M+).
Theor. C$_{15}$H$_{19}$NO$_5$.⅜H$_2$O: C, 60.04; H, 6.63; N, 4.67.
Found: C, 60.03; H, 6.51; N, 4.52.

EXAMPLE 29

3-Benzyl-1-(1,3-dioxolan-2-yl)-1,5-epoxy-1,2,4,5-tetrahydro-3-benzazepin

A stirred mixture of 2-furfural (132 g, 1.375M), ethylene glycol (97 g, 1.565M) and p-toluenesulfonic acid (0.40 g, 2.1 mM) in dry benzene (350 ml) was refluxed for five hours with azeotropic removal of water (Dean-Stark trap). After 25 ml of water had been collected, the mixture was cooled, diluted with ether and filtered through Celite. The filtered solution was washed successively with saturated sodium bicarbonate solution, water and saturated NaCl solution, dried over anhydrous K₂CO₃ and concentrated in vacuo. Distillation of the residue gave the dioxolanyl furan (147.3 g, 76% yield), bp 58° C., 0.7 mm.

2-Bromofluorobenzene (36.0 g, 0.222M) in THF (200 ml) was added dropwise over one hour to a refluxing mixture of the above furan (28.0 g, 0.200M) and magnesium turnings (5.4 g, 0.206M) in dry THF (200 ml) under nitrogen. After the addition was complete, refluxing was continued for one hour. The cooled mixture was then poured onto saturated NH₄Cl solution (250 ml), the organic layer separated and the aqueous layer re-extracted with ether. The combined organic extract was washed with saturated NH₄Cl solution, dried over anhydrous K₂CO₃-Na₂SO₄ and concentrated in vacuo. The residue was purified on the Waters Prep 500 HPLC using two columns and eluting with EtOAc/hexane (1:4). A total of 33.3 g of 1-(1,3-dioxolan-2-yl)-1,4-epoxy-1,4-dihydronaphthalene was obtained as a pale yellow oil. Crystallization of the oil from hexane gave 32.5 g (75% yield) as white crystals, mp 48°–49° C.

Ozone was passed into a solution of the olefin (21.6 g, 0.10M) in methanol (300 ml) at −78° C. (dry ice-acetone bath) until a pale blue color was obtained (approximately one hour). Nitrogen was then passed into the solution to discharge the blue color and Me₂S (38 ml, 0.517M) was added. After stirring at −78° C. for 30 minutes, 0° C. (ice bath) for 30 minutes, and room temperature for 30 minutes, the methanol was removed in vacuo.

The residue was taken up in dry THF (200 ml) and added dropwise to a suspension of LiAlH₄ (10.0 g, 0.263M) in dry THF (200 ml). The reaction was strongly exothermic, causing the solvent to reflux when the addition was about half complete. When the addition was complete, the mixture was refluxed (with external heating) for 1.5 hours. The mixture was cooled in an ice bath and treated successively with distilled water (10 ml), 15% NaOH solution (10 ml) and water (30 ) in a dropwise manner. The resulting white suspension was filtered through Celite, the filtrate washed thoroughly with THF, and the combined washings concentrated in vacuo. The residue (23.9 g) was crystallized from ether and EtOAc to give the diol (19.25 g, 76.4% yield) as white crystals, mp 115°–116° C.

A solution of methanesulfonyl chloride (3.2 ml, 41.3 mM) in CH₂Cl₂ (25 ml) was added dropwise to a solution of the diol (5.0 g, 19.8 mM) and triethylamine (7.5 m., 54.2 mM) in CH₂Cl₂ (50 ml) at 0° C. (ice bath). When the addition was complete, the mixture was stirred at 0° C. for 15 minutes and then poured onto ice containing 30 ml of 2N HCl solution. The organic layer was separated, washed wth saturated NaCl solution, dried over anhydrous Na₂SO₄ and solvent removed in vacuo to give crude dimesylate. NMR (CDCl₃) δ 2.93 ppm (s, 3H, —OSO₂CH₃), 3.00 (s, 3H, —OSO₂CH₃), 3.90 (broad m, 4H, —OCH₂CH₂O—), 4.43 (d, 2H, J=5 Hz, —CH—CH₂OSO₂CH₃), 4.57 (s, 2H,

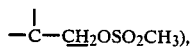
—C—CH₂OSO₂CH₃), 5.13 (s, 1H, —OCHO—), 5.57 (t, 1H, J=5 Hz, —CH—CH₂OSO₂CH₃), 7.35 (s, 4H, aromatic).

The crude dimesylate was treated with freshly distilled benzylamine (10.0 ml, 91.7 mM) and heated at 100° C. for 1.5 hours under nitrogen. The excess benzylamine was distilled in vacuo and the residue partitioned between CH₂Cl₂ and distilled water. The CH₂Cl₂ extract was then dried over anhydrous Na₂SO₄ and concentrated in vacuo to give crude amino-mesylate. NMR (CDCl₃) δ 2.77 ppm (s, 3H, —OSO₂CH₃), 2.93 (m, 2H,

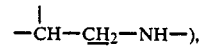
—CH—CH₂—NH—), 2.13 (broad s, 1H, —NH—), 3.80 (m, 6H, —OCH₂CH₂O— and PhCH₂—NH—), 4.53 (s, 2H, —CH₂—OSO₂CH₃), 5.10 (s, 1H, —OCHO—), 5.43 (dd, 1H, J=4, 6 Hz), 7.26 (s, 4H, aromatic).

The crude amino-mesylate was dissolved in DMF (50 ml), treated with finely powdered anhydrous K₂CO₃ (20.0 g, 0.145M) and refluxed for two hours under nitrogen. The cooled mixture was diluted with ether and filtered. The filtered solution was then washed with several portions of distilled water and the combined aqueous washings re-extracted withe ether. The combined ether extract was washed with saturated NaCl solution, dried over anhydrous K₂CO₃ and ether removed in vacuo. The residue was purified by column chromatography on 150 g silica gel and eluted with EtOAc/hexane (1:4). Pure named compound (5.6 g, 87% yield from the diol) was thus isolated as a pale yellow oil. The oil was crystallized from hexane to give analytically pure product (5.1 g) as white crystals, mp 78.0°–79.5° C. NMR (CDCl₃) δ 2.70 ppm (m, 4H, —CH₂—N(CH₂Ph)—CH₂—), 3.50 (s, 2H, —NCH₂Ph), 4.00 (m, 4H, —OCH₂CH₂O—), 5.13 (s, 2H, —CH—CH₂N and OCHO—), 6.70–7.20 (m, 9H, aromatic).

Theor. C₂₀H₂₁O₃N: C, 74.28; H, 6.55; N, 4.33. Found: C, 74.40; H, 6.67; N, 4.28.

EXAMPLE 30

1-(1,3-Dioxolan-2-yl)-1,5-epoxy-1,2,4,5-tetrahydro-3-benzazepin

A suspension of 10% Pd-C (900 mg) in a solution of the product from Example 29 (6.0 g, 18.58 mM) and glacial acetic acid (7.5 ml) in absolute ethanol (75 ml) was hydrogenated in a Parr apparatus at an initial pressure of 20 psi. After two hours, the catalyst was filtered through Celite and solvents removed in vacuo. The residue was made basic with saturated NaHCO₃ solution and extracted with Et₂O. The Et₂O extracts were discarded, and the aqueous solution evaporated to dryness. The white solid residue was washed thoroughly with CH₂Cl₂ on a sintered glass funnel. The CH₂Cl₂ washings were evaporated to dryness, the residue again taken up in CH₂Cl₂, dried (Na₂SO₄) and evaporated. The residue (3.70 g, 85.5% yield) was crystallized from hexane to give the named compound (3.45 g. 80% yield) as white crystals, mp 105.5°–107.5° C. NMR (CDCl₃) δ 1.50 (broad s, 1H, NH), 2.30–3.50 (m, 4H, —CH₂NHCH₂—), 4.00 (m, 4H, —OCH₂CH₂O—), 5.13 (s, 2H,

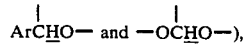
ArCHO— and —OCHO—), 7.30 (m, 4H, aromatic), IR (KBr) 3320 cm⁻¹ (NH).
Theor. C₁₃H₁₅NO₃: C, 66.94; H, 6.48; N, 6.00. Found: C, 65.95; H, 6.49; N, 5.86.

EXAMPLE 31

3-Acetyl-1-(1,3-dioxolan-2-yl)-1,5-epoxy-1,2,4,5-tetrahydro-3-benzazepin

A suspension of 10% Pd-C (1.42 g) in a solution of the product from Example 29 (9.75 g, 0.0302M) and glacial acetic acid (12 ml) in absolute ethanol (130 ml) was hydrogenated in a Parr apparatus at an initial pressure of 32 psi. After six hours, the catalyst was removed by filtration through Celite and the solvents. removed in vacuo. The residue was taken up in CH$_2$Cl$_2$ (50 ml) and treated with acetic anhydride (6.0 ml). After 15 minutes, the mixture was evaporated to dryness and the residue crystallized from Et$_2$O to give the titled compound (7.34 g, 88% yield) as white crystals, mp 122°–123° C. NMR (CDCl$_3$) δ 1.73 ppm (s, 3H, COC$\underline{H}_3$), 3.0–4.60 (m, 8H,

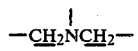

and —OC$\underline{H}_2$CH$_2$O—), 5.17 (m, 2H,

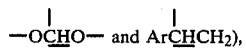

7.25 (m, 4H, aromatic $\underline{H}$). IR (KBr): 1653 cm$^{-1}$ (C=O). MS: 275 (M+).

Theor. C$_{15}$H$_{17}$NO$_4$: C, 65.44; H, 6.22; N, 5.09. Found: C, 65.46; H, 6.28; N, 4.89.

EXAMPLE 32

3-Ethyl-1-(1,3-dioxolan-2-yl)-1,5-epoxy-1,2,4,5-tetrahydro-3-benzazepin

To a suspension of LiAlH$_4$ (910 mg, 23.95 mM) in dry THF (40 ml) under N$_2$, was added the product from Example 31 (2.01 g, 7.31 mM) in one portion and the resulting mixture refluxed for one hour. The mixture was then cooled in an ice bath and treated successively with distilled water (0.9 ml), 15% NaOH solution (0.9 ml) and water (2.7 ml) in a dropwise manner. The resulting white suspension was filtered through Celite, the filtered cake washed thoroughly with THF, and the combined washings concentrated in vacuo. The residue was crystallized from Et$_2$O-hexane to give the named compound (1.81 g, 95% yield) as white crystals, mp 107°–108° C. NMR (CDCl$_3$) δ 0.87 ppm (t, 3H, J=7 Hz, NCH$_2$C$\underline{H}_3$), 2.38 (q, 2H, J=7 Hz, NC$\underline{H}_2$CH$_3$), 2.52 (AB doublet, 1H, J=11 Hz, ArCC$\underline{H}_2$), 2.67 (m, 2H, ArCHC$\underline{H}_2$), 2.87 (AB doublet, 1H, J=11 Hz, ArCC$\underline{H}_2$), 4.00 (m, 4H, OC$\underline{H}_2$C$\underline{H}_2$O), 5.20 (m, 2H, ArC$\underline{H}$CH$_2$ and OC$\underline{H}$O—), 7.20 (m, 4H, aromatic $\underline{H}$). MS: 261 (M+).

Theor. C$_{15}$H$_{19}$NO$_3$: C, 68.94; H, 7.33; N, 5.36. Found: C, 68.53; H, 7.32; N, 5.30.

EXAMPLE 33

1-(1,3-Dioxolan-2-yl)-1,5-epoxy-3-[N-(3-morpholinopropyl)]-1,2,4,5-tetrahydro-3-benzazepin dioxalate A solution of the diol (6.0 g, 0.024M), prepared as described in Example 27, and triethylamine (9.96 ml, 0.072M) in CH$_2$Cl$_2$ (150 ml) at 0° C. was treated with a solution of methanesulfonyl chloride (4.64 ml, 0.060M) in CH$_2$Cl$_2$ (25 ml) in a dropwise manner. After stirring overnight, the mixture was poured onto ice containing 2N HCl, and extracted with CH$_2$Cl$_2$. The extract was washed with H$_2$O, dried (Na$_2$SO$_4$), and the solvent evaporated in vacuo to give the dimesylate (9.30 g, 96% yield).

The dimesylate was heated with N-(3-aminopropyl)-morpholine (10 ml) at 120° C. for 1.5 hours under N$_2$. Upon cooling, excess N-(3-aminopropyl)morpholine was removed in vacuo and the product was taken up in CH$_2$Cl$_2$, washed twice with H$_2$O, saturated NaCl, dried (Na$_2$SO$_4$), and evaporated. The residue was purified by column chromatography on silica gel, eluting with 2% MeOH/CH$_2$Cl$_2$, then 5% MeOH/CH$_2$Cl$_2$. Fractions containing the desired compound were combined and concentrated to give the eopxybenzazepin. A solution of oxalic acid (3.2 g, 0.026M) in ether was added dropwise to a solution of this product in ether to give the titled compound (3.9 g, 60% yield), which was recrystallized from MeOH/acetone to give a pale pink powder, mp 193°–194° C. (dec). NMR (DMSO-d$_6$) δ 2.30–3.00 ppm [m, 14H, (6x) N—CH$_2$, —CH$_2$C$\underline{H}_2$—CH$_2$—), 3.40–4.00 (m, 8H, —C$\underline{H}_2$OC$\underline{H}_2$ and —OC$\underline{H}_2$C$\underline{H}_2$O), 5.10–5.30 (m, 2H, ArC$\underline{H}$O and —O-C$\underline{H}$O), 7.27 (s, 4H, aromatic $\underline{H}$), 8.50 [broad s, 4H, (4x) CO$\underline{H}$]; IR (KBr): 3430 cm$^{-1}$ (OH), 1715 cm$^{-1}$ (CO$_2$H), 1600 cm$^{-1}$ (CO$_2^{63}$); MS: 360 (M+).

Theor. C$_{20}$H$_{28}$N$_2$O$_4$·C$_4$H$_4$O$_8$: C, 53.33; H, 5.97; N, 5.18. Found: C, 52.73; H, 6.00; N, 4.95.

EXAMPLE 34

3-Benzyl-7,8-dimethoxy-1,5-epoxy-1,2,4,5-tetrahydro-3-benzazepin

A solution of veratrole (28.0 ml, 0.22M) in 95% ethanol (75 ml) was heated to 60° C. and, while stirring, was treated with iodine (50 g, 0.197M) and yellow mercuric oxide (30.0 g, 0.1385M). The iodine and mercuric oxide were added alternately in small portions over a period of 1.5 hours. After the addition was complete, the cooled mixture was filtered through Celite and concentrated. The residue was taken up in Et$_2$O and again filtered. The Et$_2$O solution was washed with solutions of sodium thiosulfate, 2N NaOH, saturated NaCl, dried over anhydrous K$_2$CO$_3$ and evaporated. The residue was distilled under reduced pressure to give 40.88 g, bp 110°–112° C. (2mm) pure 4-iodoveratrole [70% yield, literature: Gutzke et al., *J. Org. Chem.* 22, 1271 (1957), bp 80°–85° C. (1 mm)]. NMR (CDCl$_3$) δ 3.80 ppm (s, 6H, (2x) OC$\underline{H}_3$), 6.57 (d, 1H, ArH$_6$), 7.20 (m, 2H, ArH$_3$ and ArH$_5$).

4-Iodoveratrole (26.0 g, 0.0985M) in acetic acid (25 ml) was treated with bromine (6.5 ml, 0.127M) in acetic acid (30 ml) and stirred at room temperature for one hour. The mixture was diluted with water (300 ml) and treated with sodium bisulfite to discharge the excess bromine. The white solid was filtered, washed with water and dried in vacuo over P$_2$O$_5$ to give 4-bromo-5-iodoveratrole (33.0 g, 95% yield) as a white solid, mp 98°–100° C. (literature: Baker et al., *J. Chem. Soc.* 3986 (1961), mp 102°–104° C.). NMR (CDCl$_3$) δ 3.83 ppm (s, 6H, (2x) OC$\underline{H}_3$), 7.06 (s, 1H, Ar$\underline{H}$), 7.21 (s, 1H, Ar$\underline{H}$).

A solution of this compound (22.38 g, 0.065M) in a mixture of furan (100 ml) and anhydrous ether (100 ml) at −78° C. (dry ice-acetone bath) under nitrogen was treated dropwise via syringe with n-BuLi (29.0 ml, 2.45M in hexane, 0.071M) over a period of 20 minutes. After two hours at −78° C., the mixture was allowed to warm to room temperature and stirred for an additional 2.5 hours. The mixture was then poured onto saturated NH₄Cl solution and extracted with CH₂Cl₂. The combined extracts were dried over anhydrous Na₂SO₄ and evaporated. The residue was crystallized from Et₂O/hexane (ca. 1:1) to give the olefin (8.39 g, 63% yield) as white crystals, mp 152°-154° C. NMR (CDCl₃) δ 3.83 ppm (s, 6H, (2x) OC$\underline{H}$₃), 5.65 (broad s, 2H,

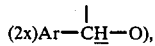
(2x)Ar—C$\underline{H}$—O), 6.96 (m, 4H, —C$\underline{H}$=C$\underline{H}$— and aromatic $\underline{H}$) MS: 204 (M+).

Ozone was passed into a solution of the olefin (12.64 g, 0.062M) in a mixture of CH₂Cl₂ (250 ml) and MeOH (250 ml) at −78° C. (dry ice/acetone bath) until a pale blue color was obtained. Nitrogen was then passed into the solution to discharge the blue color and Me₂S (20 ml, 0.277M) was added. After stirring at −78° C. for 45 minutes, 0° C. (ice bath) for 30 minutes, and room temperature for 30 minutes, the solvents were removed in vacuo. Benzene (100 ml) was added to the residue and again evaporated to dryness. The residue was taken up in dry THF (150 ml) and added dropwise to a suspension of LiAlH₄ (7.20 g, 0.189M) in dry THF (150 ml). When the addition was complete, the mixture was refluxed for 45 minutes, cooled in an ice bath and treated successively with distilled water (7.2 ml), 15% NaOH solution (7.2 ml) and water (21.6 ml) in a dropwise manner. The resulting white suspension was filtered through Celite, the filtrate washed thoroughly with THF, and the combined washings concentrated in vacuo. The residue (9.47 g) was recrystallized from EtOAc to give the diol (4.53 g, 30.5% yield) as white needles, mp 142°-143° C. NMR (CDCl₃) δ 3.43 ppm (broad s, 2H, (2x)O$\underline{H}$), 4.90 (broad s, 10H, (2x)C$\underline{H}$₂OH and (2x)OC$\underline{H}$₃), 5.23 (broad s, 2H,

(2x)ArC$\underline{H}$O—), 6.67 (s, 2H, aromatic). MS: 240 (M+).

A solution of methanesulfonyl chloride (3.50 ml, 0.0452M) in CH₂Cl₂ (15 ml) was added dropwise to a solution of the diol (4.28 g, 0.0178M) and triethylamine (7.40 ml, 0.0535M) in CH₂Cl₂ (50 ml) at 0° C. (ice bath). After 30 minutes, the mixture was poured into ice containing 30 ml of 2N HCl solution and extracted with CH₂Cl₂. The CH₂Cl₂ extracts were washed with water, dried over anhydrous Na₂SO₄, and solvent removed in vacuo to give crude dimesylate (7.06 g, 100% yield).

The crude dimesylate was treated with freshly distilled benzylamine (15 ml) and heated at 100° C. under nitrogen for 45 minutes. The excess benzylamine was distilled in vacuo and the residue partitioned between CH₂Cl₂ and distilled water.

The CH₂Cl₂ extract was washed with H₂O, dried over anhydrous Na₂SO₄ and evaporated. The residue was purified by column chromatography on 180 g of SilicAR 7 eluted with Et₂O/hexane (1:2) to give pure titled compound (4.76 g, 86% yield from the diol) as white crystals, mp 103°-104° C, after crystallization from hexane. NMR (CDCl₃) δ 2.67 ppm (d, 4H, J=2 Hz,

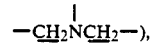
—C$\underline{H}$₂NC$\underline{H}$₂—), 3.50 (s, 2H, —C$\underline{H}$₂Ph), 3.88 (s, 6H, (2x) OC$\underline{H}$₃), 502 (broad t, 2H, J=2 Hz

(2x)ArC$\underline{H}$O—), 6.70-7.30 (m, 7H, aromatic). MS: 311 (M+).
Theor. C₁₉H₂₁NO₃: C, 73.29; H, 6.80; N, 4.50. Found: C, 72.88; H, 6.60; N, 4.19.

EXAMPLE 35

7,8-Dimethoxy-1,5-epoxy-1,2,4,5-tetrahydro-3-benzazepin

A suspension of 10% Pd-C (940 mg) in a solution of the product from Example 34 (3.20 g, 10.29 mM) and glacial acetic acid (6.5 ml) in absolute ethanol (65 ml) was hydrogenated in a Parr apparatus at an initial pressure of 35 psi. After two hours, the mixture was filtered through Celite and the solvents removed in vacuo. The residue was made basic with saturated NaHCO₃ solution and extracted with six portions of CH₂Cl₂. The combined extracts were dried over Na₂SO₄ and evaporated. The residue was recrystallized from EtOH-hexane to give pure named compound (2.07 g, 91% yield) as white needles, mp 155°-156° C. NMR (CDCl₃) δ 1.45 ppm (broad s, 1H, >N$\underline{H}$), 2.50 (AB doublet, 2H, J=13 Hz,

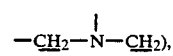
—C$\underline{H}$₂—N—C$\underline{H}$₂), 3.27 (broad AB doublet, 2H, J=13 Hz,

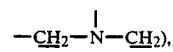
—C$\underline{H}$₂—N—C$\underline{H}$₂), 3.87 [s, 6H, (2x) OC$\underline{H}$₃], 4.90 [broad s, 2H,

(2x)ArC$\underline{H}$O—], 6.75 (s, 2H, aromatic $\underline{H}$). IR (KBr): 3340 cm⁻¹ (NH). MS: 221 (M+).
Theor. C₁₂H₁₅NO₃: C, 65.14; H, 6.83; N, 6.33. Found: C, 64.85; H, 6.62; N, 6.39.

EXAMPLE 36

3-[2-[[[5-(Dimethylamino)methyl-2-furanyl]methylthio]ethyl]-1,5-epoxy-7,8-dimethoxy-1,2,4,5-tetrahydro-3-benzazepin dioxalate monohydrate To a solution of the diol (3.70 g, 0.015M), prepared as described in Example 34 in CH₂Cl₂ (35 ml) and Et₃N (4.54 g, 0.044M), stirred at 0° C. under N₂, was slowly added methanesulfonyl chloride (4.27 g, 0.038M) in CH₂Cl₂ (25 ml). After stirring for 45 minutes at 0° C, 2N HCl (20 ml) was added to the cooled reaction mixture, the organic layer was washed with H₂O and dried (Na₂SO₄). Evaporation of solvent gave 5.52 g crude dimesylate (oil) to which was added 2-[(5-dimethylaminomethyl-2-furanyl)methylthio]ethylamine (5.5 g, 0.028M), prepared as described in Belgian Pat. No. 857,388. The reaction mixture (neat) was heated under $N_2$ at 130° C. for five hours, dissolved in $Et_2O$, washed with $H_2O$, and dried ($MgSO_4$). Solvent was evaporated in vacuo and the crude product chromatographed (silica gel, 5% $MeOH/CH_2Cl_2$) to give 960 mg (16% yield) of the epoxybenzazepin as a yellow oil.

This product (700 mg, 0.0018M) was dissolved in $Et_2O$, heated and filtered. To this solution was added oxalic acid (340 mg. 0.0038M) in $Et_2O$, and the resultant crystals were recrystallized several times from methanol/$Et_2O$ to give 470 mg (46% yield) white crystalline named compound mp 110° C. IR (KBr) 3410, 1710, 1610 $cm^{-1}$; NMR (DMSO-$d_6$) δ 6.95 (s, 2H, ArH), 6.43 (m, 2H, furan-H), 5.15 (br, 2H, ArCHO), 4.23 (s, 2H, furan-$CH_2N$), 3.76 (s, 6H, (2x) $OCH_3$), 3.66 (s, 2H, $SCH_2$-furan), 3.00 (br, 4H, $OCCH_2NCH_2CO$), 2.72 (s, 6H, $NCH_3$), 2.72-2.40 (br, 4H, $NCH_2CH_2S$); MS: 418 (M+).

For $C_{22}H_{30}N_2O_4S \cdot C_4H_4O_8 \cdot H_2O$: Theor. C, 50.64; H, 5.88; N, 4.54. Found: C, 50.23; H, 5.58; N, 4.68.

EXAMPLE 37

3-Benzyl-1,5-epoxy-7,8methylenedioxy-1,2,4,5-tetrahydro-3-benzazepin oxalate

To a solution of 1,2-methylenedioxybenzene (24.4 g, 0.20M) in AcOH (30 ml) was added ICl (40 g, 0.250M) in AcOH (50 ml) at room temperature over 0.5 hour. The reaction mixture was stirred for an additional three hours, then poured into $H_2O$ and extracted twice with ether. The organic extracts were washed with $NaHSO_3$, saturated $NaHCO_3$, $H_2O$, dried ($MgSO_4$), and evaporated in vacuo. The product was distilled under vacuum at 70' C. to give 3,4-methylenedioxyiodobenzene as a pale orange liquid (28.8 g, 57% yield). NMR ($CDCl_3$) δ 5.85 (s, 2H, O—$CH_2$—O), 6.50 (d, 1H, J=8 Hz, $H_6$), 7.10 (m, 2H, J=8 Hz, J=2 Hz, $H_2$ and $H_5$); MS: 248 (M+).

To a solution of this product (28.1 g, 0.113M) and sodium acetate (9.3 g, 0.113M) in AcOH (100 ml) at 0° C., $Br_2$ (7.2 ml, 0.14M) in AcOH (30 ml) was added dropwise. When the addition was complete, the reaction mixture was stirred at room temperature for three hours, then poured onto ice and treated with saturated $NaHSO_3$, and the solid filtered and washed with $H_2O$. The product was dried in vacuo to give 4,5-methylenedioxy-2-iodobromobenzene (35.8 g, 96% yield). NMR ($CDCl_3$) δ 5.95 ppm (s, 2H, O—$CH_2$—O), 7.0 (s, 1H, $H_3$), 7.2 (s, 1H, $H_6$); MS: 326:328 (M+).

A suspension of this compound (49 g. 0.150M) in furan (200 ml) and $Et_2O$ (200 ml) under $N_2$ at −78° C. (dry ice/acetone bath) was treated with n-BuLi (72 ml, 0.165M) in a dropwise manner over 15 minutes and stirred at −78° C. for three hours, then at room temperature for two hours. The reaction mixture was then quenched with $NH_4Cl$, extracted with ether, washed with $H_2O$, dried ($Na_2SO_4$), evaporated in vacuo, and recrystallized from EtOAc/hexane to give the olefin (27.61 g, 98% yield), NMR ($CDCl_3$) δ 5.65 ppm [s, 2H,

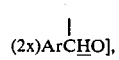
(2x)ArCHO], 5.95 (m, 2H, O—$CH_2$—O), 6.85 (s, 2H, —CH=CH—), 7.15 (s, 2H, aromatic H). MS: 188 (M+).

Ozone was passed through a solution of the olefin (6.40 g, 0.034M) in $CH_2Cl_2$ (200 ml) at −78° C. (dry ice/acetone bath) until a white solid began to precipitate. The solution was then transferred by cannulus to a solution of $LiAlH_4$ (3.24 g, 0.085M) in 150 ml dry THF at 0° C. (ice bath) under $N_2$. When the addition was complete, the mixture was refluxed for three hours. It was cooled in an ice bath and treated successively with distilled $H_2O$ (3.2 ml), 15% NaOH solution (3.2 ml), and $H_2O$ (9.6 ml) in a dropwise manner. The resulting suspension was filtered through Celite, washed with THF, and the washings dried ($Na_2SO_4$) and concentrated in vacuo. The product was collected with ether to give the diol (2.85 g, 37% yield). NMR ($CDCl_3$) δ 2.95 ppm [broad s, 2H, (2x) —$CH_2$—OH]3.60-4.25 [m, 4H, (2x) —$CH_2OH$], 5.25 [broad s, 2H,

(2x)ArCHO], 6.0 (s, 2H, O—$CH_2$—O), 6.65 (s, 2H, aromatic H). MS: 224 (M+).

A solution of methanesulfonyl chloride (5.6 ml, 0.073M) in $CH_2Cl_2$ (25 ml) was added dropwise to a solution of the diol (6.6 g, 0.029M) and triethylamine (12.0 ml, 0.087M) in $CH_2Cl_2$ (150 ml) at 0° C. After 0.5 hour, the mixture was poured onto ice containing 2N HCl, and extracted with $CH_2Cl_2$. The combined extract was washed with $H_2O$, dried ($Na_2SO_4$) and the solvent evaporated in vacuo. The product was collected with hexane to give the dimesylate (10.7 g, 97% yield). NMR (DMSO) δ 3.15 ppm [s, 6H, (2x) —$OSO_2CH_3$], 4.20-4.60 [m, 4H, (2x) —$CH_2$—OMs], 5.35 [broad s, 2H,

(2x)ArCHO], 6.05 (s, 2H, —$OCH_2O$—), 6.95 (s, 2H, aromatic H).

The dimesylate (10.6 g, 0.028M) was dissolved in benzylamine (25 ml) and heated to 100° C. under $N_2$ for three hours. Excess benzylamine was removed in vacuo and the product was taken up in $CH_2Cl_2$, washed with $H_2O$, dried ($Na_2SO_4$), and evaporated. The residue was purified by column chromatography on silica gel, eluting with $Et_2O$/hexane (1:4). Fractions containing the desired product were combined and concentrated to give the epoxybenzazepin. To a solution of this product in ether was added a solution of oxalic acid (3.88 g, 0.031M) in ether. The resulting solid was filtered and washed with ether to give the named compound (8.85 g, 82% yield), mp 231°-234° C. (dec). NMR (DMSO-$d_6$) δ 2.80 ppm (m, 4H, $CH_2$—N—$CH_2$), 3.70 (s, 2H, —N—$CH_2$—Ph), 5.10 [s, 2H,

(2x)ArCHO], 6.10 (s, 2H, O—$CH_2$—O), 6.95 (s, 2H, $H_6$ and $H_9$), 7.00-7.50 (m, 5H, —N—$CH_2$-aromatic H), 10.30 [broad s, 2H, (2x) —COOH). MS: 295 (M+).

Theor. $C_{18}H_{17}NO_3 \cdot C_2H_2O_4$: C, 62.33; H, 4.97; N, 3.63. Found: C, 62.68; H, 5.12; N, 3.75.

EXAMPLE 38

1,5-Epoxy-7,8-methylenedioxy-1,2,4,5-tetrahydro-3-benzazepin oxalate

A solution of the product prepared in Example 37 (6.6 g, 0.017M) in methanol (200 ml) and AcOH (20 ml) was hydrogenated (10% Pd-C, 0.66 g) in a Parr apparatus at an initial pressure of 40 psi overnight. The resulting solution was filtered through Celite, evaporated, and crystallized from methanol/ether to give the titled compound (2.33 g, 46% yield). The product was recrystallized from methanol/$CCl_4$ and dried in vacuo to give pure product, mp 193°–195° C. (dec). NMR (DMSO-$d_6$) δ 2.70–3.50 (m, 4H, —$CH_2$—N—$CH_2$), 5.15 [s, 2H, (2x) ArC$\underline{H}$O), 5.95 (s, 2H, —OC$H_2$O), 6.95 (s, 2H, aromatic $\underline{H}$), 7.25 (m, OH); MS: 205 ($\overline{M}$+).

Theor. $C_{11}H_{11}NO_3 \cdot C_2H_2O_4$: C, 52.89; H, 4.44; N, 4.74. Found: C, 52.83; H, 4.63; N, 4.49.

EXAMPLE 39

3-Allyl-1,5-epoxy-7,8-methylenedioxy-1,2,4,5-tetrahydro-3-benzazepin oxalate.¼$H_2O$ A solution of the diol (3.2 g, 0.014M), prepared as described in Example 37, and triethylamine (5.8 ml, 0.042M) in $CH_2Cl_2$ (150 ml) at 0° C. was treated with a solution of methanesulfonyl chloride (2.8 ml, 0.036M) in a dropwise manner. After 30 minutes, the mixture was poured onto ice containing 2N HCl, and extracted with $CH_2Cl_2$. The extract was washed with $H_2O$, dried ($Na_2SO_4$), and the solvent evaporated in vacuo to give the dimesylate.

The crude dimesylate was taken up in allylamine (20 ml) and heated in a pressure bottle at 100° C. for two hours. Upon cooling, the product was taken up in $CH_2Cl_2$ and evaporated. The residue was dissolved in $CH_2Cl_2$, washed with $H_2O$, dried ($Na_2SO_4$), and the solvent evaporated in vacuo. The residue was purified by column chromatography on silica gel, eluting with EtOAc/hexane (1:1). Fractions containing the desired product were combined and concentrated to give the epoxybenzazepin. A solution of oxalic acid (1.95 g, 0.015M) in ether was added dropwise to a solution of this product in ether to give the named compound (3.9 g, 83% yield) as a white solid which was recrystallized from hot methanol to give pure product, mp 249°–250° C. (dec). NMR (DMSO-$d_6$) δ 2.90 ppm (s, 4H, C$\underline{H_2}$—N—C$\underline{H_2}$), 3.30 (d, 2H, —C$H_2$—CH=$CH_2$), 5.00–5.50 [m, 5$\overline{H}$, (2x) ArC$\underline{H}$O, —CH=$\overline{CH_2}$], 6.0 (2s, 2H, —OCH$_2$O—), 6.95 (s, 2$\overline{H}$, aromatic $\underline{H}$); MS: 245 (M+).

For $C_{14}H_{15}NO_3 \cdot C_2H_2O_4 \cdot \frac{1}{4}H_2O$: Theor. C, 56.55; H, 5.19; N, 4.12. Found: C, 56.61; H, 5.12; N, 3.91.

EXAMPLE 40

1,5-Diphenyl-1,5-epoxy-3-[N-(3-morpholinopropyl)]-1,2,4,5-tetrahydro-3-benzazepin dioxalate hemihydrate Anthranilic acid (11.2 g, 0.082M, recrystallized from benzene) in dry THF (150 ml) was added dropwise to a refluxing solution of 2,5-diphenylfuran (15.0 g, 0.068M) and i-amylnitrite (13.7 ml, 0.051M, 50% yield) in dry THF (150 ml) under $N_2$. After the addition was complete, refluxing was continued for two hours. The reaction mixture was evaporated and the residue taken up in ether. The ether solution was washed with several portions of saturated $NaHCO_3$, $H_2O$, dried ($Na_2SO_4$) and evaporated. The residue was purified by column chromatography on neutral alumina (activity grade II), eluting with hexane, then 1:3 ether/hexane. Fractions containing the desired compound were combined and concentrated to give the olefin (15 g, 0.05M).

Ozone was passed into a solution of the olefin (15 g, 0.05M) in $CH_2Cl_2$ (250 ml) at −78° C. (dry ice/acetone bath) until a pale blue color was obtained. The solution was then transferred by cannulus to a solution of $LiAlH_4$ (4.8 g, 0.127M) in dry THF (200 ml) at 0° C. When the addition was complete, the mixture was refluxed for an additional 1.5 hours. It was cooled in an ice bath and treated successively with distilled $H_2O$ (4.8 ml), 15% NaOH (4.8 ml), and $H_2O$ (14.4 ml) in a dropwise manner. The resulting suspension was filtered through Celite, dried ($Na_2SO_4$), and concentrated in vacuo to give the diol (1.7 g as a solid, 8.6 g as liquid, 62% yield).

A solution of methanesulfonyl chloride (5.0 ml, 0.065M) in $CH_2Cl_2$ (25 ml) was added dropwise to a solution of the diol (8.6 g, 0.026M) and triethylamine (10.8 ml, 0.078M) in $CH_2Cl_2$ (150 ml) at 0° C. After 30 minutes, the mixture was poured onto ice containing 2N HCl and extracted with $CH_2Cl_2$. The extracts were washed with $H_2O$, dried ($Na_2SO_4$), and the solvent removed in vacuo. The crude dimesylate was purified by column chromatography on silica gel, eluting with 1:1 ether/hexane, to give dimesylate (11.5 g, 91% yield) as a gummy solid.

The dimesylate (2.5 g, 0.005M) was heated with N-(3-aminopropyl)morpholine (8 ml) at 140° C. for 1.5 hours under $N_2$. Upon cooling, excess N-(3-aminopropyl)morpholine was removed in vacuo and the product was taken up in $CH_2Cl_2$, washed twice with $H_2O$, saturated NaCl, dried ($Na_2SO_4$) and evaporated. The residue, $K_2CO_3$ (5 g), and DMF (20 ml) were refluxed for three hours under $N_2$. The mixture was then diluted with ether and filtered. The filtered solution was then washed twice with $H_2O$, and the combined aqueous washings re-extracted with ether. The combined ether extract was washed with saturated NaCl, dried ($K_2CO_3$), and the solvent removed in vacuo to give crude epoxybenzazepin. A solution of oxalic acid (1.16 g, 0.009M) in ether was added dropwise to a solution of this product in ether to give the named compound, which was recrystallized from MeOH and dried (0.75 g, 24% yield), mp 221°–223° C. (dec). NMR (DMSO-$d_6$) δ 1.85 (m, 2H, —$CH_2CH_2$—$CH_2$), 2.40–3.90 (m, 16H, (6x) —N—$CH_2$, —$CH_2$O$\overline{CH_2}$), 6.80–7.85 (m, 14H, aromatic $\underline{H}$), 10.10 (s, 4H, (4x) $\overline{CO_2H}$). MS: 440 (M+), 81 (BP). IR (KBr) 3420 cm$^{-1}$ (O$\underline{H}$), 1710 cm$^{-1}$ ($CO_2H$).

For $C_{29}H_{32}N_2O_2 \cdot C_4H_4O_8 \cdot \frac{1}{2}H_2O$: Theor. C, 62.95; H, 5.92; N, 4.45. Found: C, 62.66; H, 5.76; N, 4.12.

ANTI-ULCER ACTIVITY

The anti-ulcer activity of representative compounds was examined by employing five different assays, as more fully described in Examples 41–45.

EXAMPLE 41

Cytoprotection

The cytoprotective activity of the compounds was tested using a modification of the method of Robert, A., et al., *Gastroenterology* 77, 433 (1979). Basically, male Charles River Sprague Dawley derived rats weighing between 140 and 220 g were fasted overnight, but allowed water ad libitum. They were deprived of water during the experiment, however. The rats were weighed and pretreated orally with the test compound in a dose volume of 1 ml/kg. One hour later, the necrotizing agent was administered orally, usually 50% EtOH, in a dose volume of 1 ml/animal. After an additional hour, the rats were sacrificed with $CO_2$, the stomachs removed, inflated with distilled water, opened along the greater curvature and laid out on a flat surface. The presence of mucosal bleeding and incidence of lesions were noted, and after wiping off the mucosa the presence of submucosal bleeding and incidence of lesions were also noted. The results are shown in Table I.

TABLE I

| Compound (Example) | Dose (mg/kg) | % Inhibition of Lesions | |
|---|---|---|---|
| | | Mucosa | Submucosa |
| 2 | 25 | 56 | 56 |
| 4 | 10 | 70 | 80 |
| | 20 | 88 | 100 |
| 5 | 10 | 10 | 30 |
| 11 | 40 | 80 | 100 |
| 12 | 10 | 20 | 11 |

EXAMPLE 42

Gastric Secretion

The inhibitory activity of the compounds on acid output was tested using pylorus ligation in a modification of the procedure of Shay, H., et al., *Gastroenterology* 26, 906 (1954). Basically, male Charles River Sprague Dawley derived rats weighing 150-300 grams were deprived of food but not water for 18-24 hours prior to use. Water was withheld during the experiment, however. The rats were weighed, anesthetized with ether and the pylorus ligated according to the method of Shay et al., supra. Treatment or vehicle control was then administered intraduodenally (i.d.). Rats were housed two/cage and sacrificed with $CO_2$ four hours after ligation. The stomachs were removed, rinsed, and contents emptied into a graduated centrifuge tube. The tubes were centrifuged, the volume of gastric juice recorded, and any samples obviously contaminated by feces, food or blood were eliminated. A 1 ml aliquot of gastric juice was titrated with 0.1N NaOH to a pH of 7.0-7.4. The volume of gastric juice secreted, the acid concentration, and the product of the volume times the concentration, i.e., the total amount of acid secreted, were measured. The amount of the inhibition of acid output by the test compounds is shown in Table 2.

TABLE 2

| Compound (Example) | Dose (mg/kg) | % Inhibition of Gastric Secretion |
|---|---|---|
| 2 | 25 | 71 |
| 3 | 25 | 48 |
| 4 | 40 | 46 |
| 5 | 20 | 46 |
| 7 | 50 | 68 |
| 11 | 40 | 39 |
| 13 | 50 | 33 |
| 14 | 50 | 40 |
| 18 | 50 | 23 |
| 22 | 50 | 33 |
| 30 | 50 | 23 |
| 36 | 20 | 26 |

EXAMPLE 43

Gastric Secretion

This is a secondary test used to follow-up compounds which have shown gastric antisecretory activity in the four-hour pylorus ligated rat (Example 42). Female dogs were surgically prepared with total gastric fistulas and allowed to recover. Since dogs do not normally have an interdigestive gastric secretion, i.e., no basal secretion as in rats and humans, gastric secretion was stimulated with betazole. The total amount of acid secreted was determined, and the results are shown in Table 3.

TABLE 3

| Compound (Example) | Dose (mg/kg) | % Inhibition of Gastric Secretion |
|---|---|---|
| 2 | 2 (ig) | 53 |
| | 40 | 75 |
| 4 | 7.3 (iv) | 85 |
| | 20 (ig) | 48 |

EXAMPLE 44

In Vivo Pepsin Assay

Pepsin activity was measured by a radioenzymatic assay. An aliquot of a 1:1000 dilution of rat gastric juice was incubated with the substrate solution (containing methyl-$^{14}$C-methylated methemoglobin and nonradioactive methemoglobin in 0.1 mM sodium citrate buffer, pH 3.0) for a period of ten minutes at 37° C. After this time, trichloroacetic acid was added to stop the reaction and to precipitate the unreacted substrate. After removal of the precipitate by centrifugation, an aliquot of the supernatant fraction is quantitated for radioactivity by liquid scintillation spectrometry. Rat gastric juice samples were obtained after drug administration in the pylorus ligated rat (Example 42). Data is presented as the percent inhibition of pepsin activity in drug treated gastric samples compared to enzyme activity observed for control gastric juice samples. Percent inhibition of activity reflects inhibition of pepsinogen secretion into the stomach and subsequent conversion to pepsin. Results are shown in Table 4.

TABLE 4

| Compound (Example) | Dose (mg/kg) | % Inhibition of Pepsin Activity |
|---|---|---|
| 4 | 40 | 52 |
| 5 | 20 | 28-43 |
| 11 | 40 | 30 |

EXAMPLE 45

Isolated Parietal Cell Assay

The isolated parietal cell assay was conducted using the procedures of Batzri, S., et al., *Biochemica et Biophysica Acta* 508, 328 (1978) and Soll, A. H., *Am. J. Physiol.* 238, G366 (1980). Basically, parietal cells were isolated from the fundic mucosa of rabbit stomachs by a four-stage collagenase digestion process. The supernatant fraction from the last two stages of this process contain the individual parietal cells. This cell suspension was centrifuged and reconstituted in a modified Hank's buffer to contain $2-3 \times 10^6$ cells/ml. The cells in this suspension were then evaluated for their ability to accumulate $^{14}$C-aminopyrine ($^{14}$C-AP), a weak base which has been shown to accumulate in acidic environments such as the parietal cell. The accumulation was stimulated by histamine and was blocked by $H_2$ antagonists. The cells were incubated with $0.5 \times 10^6$ cpm $^{14}$C-AP, with various concentrations of histamine, $1 \times 10^{-5}$M isobutylmethylxanthine, and the test compound added in a 20 μl volume of buffer or DMSO. The flasks were incubated in a shaking water bath at 37° C. for 20 minutes. Two aliquots were then taken from each flask and cell pellets were collected by centrifugation. The pellets were solubilized with Protosol (New England Nuclear) and radioactivity determined by liquid scintillation spectrometry. Data is presented as the $IC_{50}$, the concentration of compound required to inhibit $^{14}C$-AP accumulation in the histamine stimulated parietal cell by 50%. The results are shown in Table 5.

TABLE 5

| Compound (Example) | $IC_{50}$ ($\mu M$) |
| --- | --- |
| 2 | 3.5 |
| 4 | 4.5 |
| 5 | 1–1.3 |
| 11 | 3.5 |
| 12 | 0.25–0.37 |
| 36 | 30 |

ANTIDYSRHYTHMIC ACTIVITY

The antidysrhythmic activity of representative compounds was examined as described in Example 46.

EXAMPLE 46

The antidysrhythmic activity of the compounds was tested in accordance with Baum, T. et al., *Arch. Int. Pharmacodyn.* 193, 149 (1971). Basically, adult mongrel dogs randomly selected as to sex and weight were anesthetized and a femoral artery and vein were cannulated for measuring arterial blood pressure and administering drugs, respectively. The right vagus nerve was exposed, cut, and a stimulating electrode was placed on the section leading to the heart. Lead II ECG was monitored using needle electrodes and heart rate was quantitated using a cardiotachometer triggered by the R wave of the electrocardiogram. Ouabain was injected (stat) 40 $\mu g/kg$, followed in 20 minutes by a dose of 20 $\mu g/kg$. Additional ouabain was given in doses of 10 $\mu g/kg$ at 20 minute intervals until a well-established ventricular arrhythmia (ouabain-intoxication) was observed. The test compound was then administered intravenously. Right vagal stimulation (3.5 V, 20 cps) was employed to indicate presence of normal sinus rhythm. The dosage of the compounds tested showing antidysrhythmic activity is shown in Table 6.

TABLE 6

| Compound (Example) | Dose (mg/kg, iv) |
| --- | --- |
| 2 | 18.5 |
| 7 | 6.0 |
| 16 | 3.5 |
| 18 | 18.5 |
| 19 | 18.5 |
| 27 | 18.5 |
| 30 | 8.5 |
| 35 | 3.5 |

What is claimed is:
1. A compound of the formula

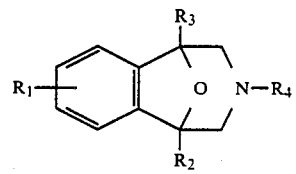

where
$R_1$ is H, 7-halogen, 7,8-dihydroxy, 7,8-methylenedioxy, 7,8-di-$C_1$-$C_3$ alkoxy or 7,8-dibenzyloxy;
$R_2$ is H, 1,3-dioxolanyl, phenyl or phenyl substituted by $CF_3$, $C_1$-$C_6$ alkyl or $C_1$-$C_4$ alkoxy;
$R_3$ is H, phenyl or phenyl substituted by $CF_3$, $C_1$-$C_6$ alkyl or $C_1$-$C_4$ alkoxy;
$R_4$ is H, benzyl, $C_1$-$C_6$ alkyl, $C_3$-$C_6$ alkenyl, —($CH_2$)$_3$OH,

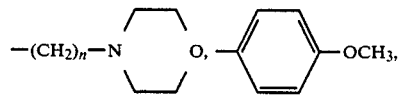

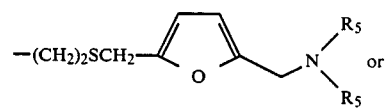

$R_5$ is $C_1$-$C_3$ alkyl; n is 2 or 3, and the oxalate and dioxalate salts thereof, provided that when $R_1$ is 7-halogen, $R_4$ is not hydrogen.
2. A compound of claim 1 wherein $R_1$ is H, $R_2$ is phenyl or 3-trifluoromethylphenyl, $R_3$ is H and $R_4$ is H,

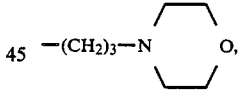

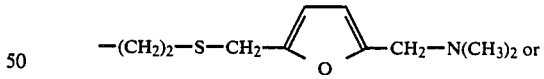

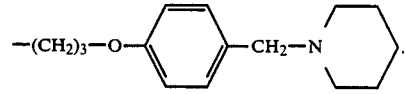

3. A compound of claim 1 selected from the group consisting of 3-benzyl-1,5-epoxy-1-[(3-trifluoromethyl)-phenyl]-1,2,4,5-tetrahydro-3-benzazepin oxalate; 1,5-epoxy-1-[(3-trifluoromethyl)phenyl]-1,2,4,5-tetrahydro-3-benzazepin oxalate; 1,5-epoxy-3-[N-(3-morpholinopropyl)]-1-[(3-trifluoromethyl)phenyl]-1,2,4,5-tetrahydro-3-benzazepin oxalate; 3-[3-[[3-(1-piperidinyl)methyl]-phenoxy]propyl]-1,5-epoxy-1-(3-trifluoromethyl)-phenyl-1,2,4,5-tetrahydro-3-benzazepin dioxalate; 3-[2-[[[5-(dimethylamino)methyl-2-furanyl]methylthio]ethyl]-1,5-epoxy-1-[3-trifluoromethyl)phenyl-1,2,4,5-tetrahydro-3-benzazepin dioxalate; 3-benzyl-1,5-epoxy-1- phenyl-1,2,4,5-tetrahydro-3-benzazepin; 1,5-epoxy-1-phenyl-1,2,4,5-tetrahydro-3-benzazepin; 3-acetyl-1,5-epoxy-1-phenyl-1,2,4,5-tetrahydro-3-benzazepin; 3-ethyl-1-phenyl-1,5-epoxy-1,2,4,5-tetrahydro-3-benzazepin; 3-allyl-1,5-epoxy-1-phenyl-1,2,4,5-tetrahydro-3-benzazepin; 3-[3-[[3-(1-piperidinyl)methyl]methyl]phenoxy]propyl]-1,5-epoxy-1-phenyl-1,2,4,5-tetrahydro-3-benzazepin dioxalate; 3-[2-[[[5-(dimethylamino)methyl-2-furanyl]methylthio]ethyl]-1,5-epoxy-1-phenyl-1,2,4,5-tetrahydro-3-benzazepin dioxalate; and 1,5-diphenyl-1,5-epoxy-3-[N-(3-morpholinopropyl)]-1,2,4,5,-tetrahydro-3-benzazepin dioxalate.

4. A compound of claim 3 selected from the group consisting of 1,5-epoxy-1-[(3-trifluoromethyl)phenyl]-1,2,4,5-tetrahydro-3-benzazepin oxalate; 1,5-epoxy-3-[N-(3-morpholinopropyl)]-1-[(3-trifluoromethyl)phenyl]-1,2,4,5-tetrahydro-3-benzazepin oxalate; 3-[3-[[3-(1-piperidinyl)methyl]-phenoxy]propyl]-1,5-epoxy-1-(3-trifluoromethyl)phenyl-1,2,4,5-tetrahydro-3-benzazepin dioxalate; 3-[2-[[[5-(dimethylamino)methyl-2-furanyl]methylthio]ethyl]-1,5-epoxy-1-[3-trifluoromethyl)phenyl-1,2,4,5-tetrahydro-3-benzazepin dioxalate; 1,5-epoxy-1-phenyl-1,2,4,5-tetrahydro-3-benzazepin; 3-[3-[[3-(1-piperidinyl)methyl]methyl]-phenoxy]-propyl]-1,5-epoxy-1-phenyl-1,2,4,5-tetrahyro-3-benzazepin dioxalate; and 3-[2-[[[5-(dimethylamino)methyl-2-furanyl]methylthio]ethyl]-1,5-epoxy-1-phenyl-1,2,4,5-tetrahydro-3-benzazepin dioxalate.

5. A compound of claim 1 selected from the group consisting of 3-benzyl-7,8-dimethoxy-1-(1,3-dioxolan-2-yl)-1,5-epoxy-1,2,4,5-tetrahydro-3-benzazepin; 7,8-dimethoxy-1-(1,3-dioxolan-2-yl)-1,5-epoxy-1,2,4,5-tetrahydro-3-benzazepin; 3-benzyl-1-(1,3-dioxolan-2-yl)-1,5-epoxy-1,2,4,5-tetrahydro-3-benzazepin; 1-(1,3-dioxolan-2-yl)-1,5-epoxy-1,2,4,5-tetrahydro-3-benzazepin; 3-acetyl-1-(1,3-dioxolan-2-yl)-1,5-epoxy-1,2,4,5-tetrahydro-3-benzazepin; 3-ethyl-1-(1,3-dioxolan-2-yl)-1,5-epoxy-1,2,4,5-tetrahydro-3-benzazepin; and 1-(1,3-dioxolan-2-yl)-1,5-epoxy-3-[N-(3-morpholinopropyl)]-1,2,4,5-tetrahydro-3-benzazepin dioxalate.

6. A compound of claim 1 selected from the group consisting of 3-allyl-7-chloro-1,5-epoxy-1,2,4,5-tetrahydro-3-benzazepin oxalate; 7-chloro-1,5-epoxy-1,2,4,5-tetrahydro-3-benzazepin oxalate; 3-benzyl-7-chloro-1,5-epoxy-1,2,4,5-tetrahydro-3-benzazepin oxalate; 3-benzyl-7,8-dibenzyloxy-1,5-epoxy-1,2,4,5-tetrahydro-3-benzazepin; 7,8-dihydroxy-1,5-epoxy-1,2,4,5-tetrahydro-3-benzazepin oxalate; 3-benzyl-1,5-epoxy-1,2,4,5-tetrahydro-3-benzazepin oxalate; 1,5-epoxy-1,2,4,5-tetrahydro-3-benzazepin oxalate; 1,5-epoxy-3-propyl-1,2,4,5-tetrahydro-3-benzazepin oxalate; 1,5-epoxy-3-ethyl-1,2,4,5-tetrahydro-3-benzazepin oxalate; 1,5-epoxy-3-[N-(3-morpholinopropyl)]-1,2,4,5-tetrahydro-3-benzazepin dioxalate; 1,5-epoxy-3-[N-(2-morpholinoethyl)]-1,2,4,5-tetrahydro-3-benzazepin dioxalate; 3-allyl-1,5-epoxy-1,2,4,5-tetrahydro-3-benzazepin oxalate; 1,5-epoxy-3-[(4'-methoxy)phenyl]-1,2,4,5-tetrahydro-3-benzazepin; 1,5-epoxy-3-(3-hydroxypropyl)-1,2,4,5-tetrahydro-3-benzazepin; 3-benzyl-7,8-dimethoxy-1,5-epoxy-1,2,4,5-tetrahydro-3-benzazepin; 7,8-dimethoxy-1,5-epoxy-1,2,4,5-tetrahydro-3-benzazepin; 3-[2-[[[5-(dimethylamino)methyl-2-furanyl]methylthio]ethyl]-1,5-epoxy-7,8-dimethoxy-1,2,4,5-tetrahydro-3-benzazepin dioxalate; 3-benzyl-1,5-epoxy-7,8-methylenedioxy-1,2,4,5-tetrahydro-3-benzazepin oxalate; 1,5-epoxy-7,8-methylenedioxy-1,2,4,5-tetrahydro-3-benzazepin oxalate; and 3-allyl-1,5-epoxy-7,8-methylenedioxy-1,2,4,5-tetrahydro-3-benzazepin oxalate.

7. A method of inducing cytoprotection in mammals by increasing the natural integrity of the gastrointestinal mucosa which comprises administering to a mammal an effective amount of a compound of claim 1.

8. A method of inhibiting gastric secretion in mammals which comprises administering to a mammal an effective amount of a compound of claim 1.

* * * * *